United States Patent
Sims et al.

(10) Patent No.: US 7,585,949 B2
(45) Date of Patent: Sep. 8, 2009

(54) IL-1 ZETA SPLICE VARIANT POLYPEPTIDE

(75) Inventors: John E. Sims, Seattle, WA (US); Dirk E. Smith, Bainbridge Island, WA (US); Teresa L. Born, Kenmore, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 11/717,859

(22) Filed: Mar. 13, 2007

(65) Prior Publication Data

US 2007/0172456 A1    Jul. 26, 2007

Related U.S. Application Data

(60) Division of application No. 10/888,867, filed on Jul. 9, 2004, now Pat. No. 7,217,540, which is a division of application No. 09/876,790, filed on Jun. 6, 2001, now Pat. No. 7,033,783, which is a continuation-in-part of application No. PCT/US99/29549, filed on Dec. 14, 1999.

(60) Provisional application No. 60/164,675, filed on Nov. 10, 1999, provisional application No. 60/112,163, filed on Dec. 14, 1998.

(51) Int. Cl.
*C07K 14/705* (2006.01)
*C12P 21/02* (2006.01)

(52) U.S. Cl. .............. 530/351; 435/69.1; 435/69.7; 536/23.5

(58) Field of Classification Search .............. None
See application file for complete search history.

(56) References Cited

U.S. PATENT DOCUMENTS

| 6,117,654 | A | 9/2000 | Pan |
| 6,342,371 | B1 | 1/2002 | McDonnell et al. |
| 6,680,380 | B1 | 1/2004 | Timans |

FOREIGN PATENT DOCUMENTS

| EP | 1092773 A2 | 4/2001 |
| WO | WO 99/06426 | 2/1999 |
| WO | WO 00/17363 | 3/2000 |
| WO | WO 00/24899 | 5/2000 |
| WO | WO 00/39297 | 7/2000 |
| WO | WO 00/63226 | 10/2000 |

OTHER PUBLICATIONS

Carrié, A. et al., "A new member of the IL-1 receptor family highly expressed in hippocampus and involved in X-linked mental retardation," *Nature Genetics* 23:25-31, 1999.
Dinarello, C.A., "Biologic basis for interleukin-1 in disease," *Blood* 87(6):2095-2147, 1996.
Genbank Accession No. AL031466, XP002389791, Sep. 7, 1998.
Genbank Accession No. AL031575, XP002389792, Sep. 17, 1998.
EMBL Accession No. AC005748, XP002389794, Oct. 5, 1998.
EMBL Accession NO. AJ243874, XP002389793, Sep. 15, 1999.
Wells, 1990, Biochemistry 29:8509-8517.

*Primary Examiner*—Bridget E Bunner
*Assistant Examiner*—Fozia M Hamud
(74) *Attorney, Agent, or Firm*—Mark K Hehman

(57) ABSTRACT

The invention is directed to novel, purified and isolated IL-1 zeta and Xrec2 polypeptides and fragments thereof, the nucleic acids encoding such polypeptides, processes for production of recombinant forms of such polypeptides, antibodies generated against these polypeptides, fragmented peptides derived from these polypeptides, and uses thereof.

4 Claims, 1 Drawing Sheet

IL-1 ZETA SPLICE VARIANT POLYPEPTIDE

CROSS REFERENCE TO RELATED APPLICATIONS

This application is a divisional of U.S. patent application Ser. No. 10/888,867, filed Jul. 9, 2004, now allowed, which is a divisional of U.S. patent application Ser. No. 09/876,790, filed Jun. 6, 2001, issued as U.S. Pat. No. 7,033,783 on Apr. 25, 2006, which is a continuation-in-part of International Application PCT/US99/29549, with an international filing date of Dec. 14, 1999 and published in English on Jun. 22, 2000; and claims the benefit of U.S. provisional Application 60/164,675, filed on Nov. 10, 1999, and U.S. Provisional Application 60/112,163, filed Dec. 14, 1998.

BACKGROUND OF THE INVENTION

1. Field of the Invention

The invention is directed to novel, purified and isolated IL-1 zeta, IL-1 zeta splice variants and Xrec2 polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

Interleukin-1 (IL-1) is a member of a large group of cytokines whose primary function is to mediate immune and inflammatory responses. There are five known IL-1 family members which include IL-1 alpha (IL-1α), IL-1 beta (IL-1β), IL-1 receptor antagonist (IL-1ra), IL-1 delta (IL-1δ) as disclosed in US/99/00514), and IL-18 (previously known as IGIF and sometimes IL-1 gamma). IL-1 that is secreted by macrophages is actually a mixture of mostly IL-1β and some IL-1α (Abbas et al., 1994). IL-1α and IL-1β, which are first produced as 33 kD precursors that lack a signal sequence, are further processed by proteolytic cleavage to produce secreted active forms, each about 17 kD. Additionally, the 33 kD precursor of IL-1α is also active. Both forms of IL-1 I are the products of two different genes located on chromosome 2. Although the two forms are less than 30 percent homologous to each other, they both bind to the same receptors and have similar activities.

IL-1ra, a biologically inactive form of IL-1, is structurally homologous to IL-1 and binds to the same receptors. Additionally, IL-1ra is produced with a signal sequence which allows for efficient secretion into the extracellular region where it competitively competes with IL-1 (Abbas et al., 1994).

The IL-1 family of ligands binds to a family of two IL-1 receptors, which are members of the Ig superfamily. IL-1 receptors include the 80 kDa type I receptor (IL-1RI) and a 68 kDa type II receptor (IL-1RII). IL-1 ligands can also bind to a soluble proteolytic fragment of IL-1RII (sIL-1RII) (Colotta et al., 1993).

The major source of IL-1 is the activated macrophage or mononuclear phagocyte. Other cells that produce IL-1 include epithelial and endothelial cells (Abbas et al., 1994). IL-1 secretion from macrophages occurs after the macrophage encounters and ingests gram-negative bacteria. Such bacteria contain lipopolysaccharide (LPS) molecules, also known as endotoxin, in the bacterial cell wall. LPS molecules are the active components that stimulate macrophages to produce tumor necrosis factor (TNF) and IL-1. In this case, IL-1 is produced in response to LPS and TNF production. At low concentrations, LPS stimulates macrophages and activates B-cells and other host responses needed to eliminate the bacterial infection; however, at high concentrations, LPS can cause severe tissue damage, shock, and even death.

The biological functions of IL-1 include activating vascular endothelial cells and lymphocytes, local tissue destruction, and fever (Janeway et al., 1996). At low levels, IL-1 stimulates macrophages and vascular endothelial cells to produce IL-6, upregulates molecules on the surface of vascular endothelial cells to increase leukocyte adhesion, and indirectly activates inflammatory leukocytes by stimulating mononuclear phagocytes and other cells to produce certain chemokines that activate inflammatory leukocytes. Additionally, IL-1 is involved in other inflammatory responses such as induction of prostaglandins, nitric oxide synthetase, and metalloproteinases. These IL-1 functions are crucial during low level microbial infections. However, if the microbial infection escalates, IL-1 acts systemically by inducing fever, stimulating mononuclear phagocytes to produce IL-1 and IL-6, increasing the production of serum proteins from hepatocytes, and activating the coagulation system. Additionally, IL-1 does not cause hemorrhagic necrosis of tumors, suppress bone marrow stem cell division, and IL-1 is lethal to humans at high concentrations.

Given the important function of IL-1, there is a need to identify additional members of the IL-1 ligand family and the IL-1 receptor family. In addition, in view of the continuing interest in protein research and the immune system, the discovery, identification, and roles of new proteins and their inhibitors, are at the forefront of modern molecular biology and biochemistry. Despite the growing body of knowledge, there is still a need in the art to discover the identity and function of proteins involved in cellular and immune responses.

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, *Biology of Microorganisms* 76-77 (Prentice Hall, 6d ed. 1991)). Protein molecular weight standards are commercially available to assist in the estimation of molecular weights of unknown protein (New England Biolabs Inc. Catalog:130-131, 1995; J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., *J. Biol. Chem.* 252:1102-1106, 1977; M. Brown et al., *J. Gen. Virol.* 50:309-316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, *Biology of Microorganisms* 76-77 (Prentice Hall, 6d ed. 1991)).

Fragmentation of proteins is further employed for amino acid composition analysis and protein sequencing (P. Matsudiara, *J. Biol. Chem.* 262:10035-10038, 1987; C. Eckerskom et al., *Electrophoresis* 1988, 9:830-838, 1988), particularly the production of fragments from proteins with a "blocked" N-terminus. In addition, fragmented proteins can be used for immunization, for affinity selection (R. A. Brown, U.S. Pat. No. 5,151,412), for determination of modification sites (e.g. phosphorylation), for generation of active biological compounds (T. D. Brock and M. T. Madigan, *Biology of Microorganisms* 300-301 (Prentice Hall, 6d ed. 1991)), and for differentiation of homologous proteins (M. Brown et al., *J. Gen. Virol.* 50:309-316, 1980).

In addition, when a peptide fingerprint of an unknown protein is obtained, it can be compared to a database of known proteins to assist in the identification of the unknown protein using mass spectrometry (W.J. Henzel et al., *Proc. Natl. Acad. Sci. USA* 90:5011-5015, 1993; D. Fenyo et al., *Electrophoresis* 19:998-1005, 1998). A variety of computer software programs to facilitate these comparisons are accessible via the Internet, such as Protein Prospector (on the World Wide Web [www], at uscf.edu, search the site for prospector), Multildent (on the World Wide Web [www], at expasy.org, search for Multildent), PeptideSearch (on the World Wide Web [www], at mann.embl-heiedelberg.de, using the PeptideSearch link), and ProFound (as described by Zhang and Chait, *Anal. Chem.* 72:2482, 2000, available online from Rockefeller University by performing a web search on 'profound' and 'rockefeller'). These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining the number of fragmented peptides and their molecular weight should result in enhanced likelihood of success in the identification of unknown proteins.

In addition, peptide digests of unknown proteins can be sequenced using tandem mass spectrometry (MS/MS) and the resulting sequence searched against databases (J.K. Eng, et al., *J. Am. Soc. Mass Spec.* 5:976-989 (1994); M. Mann and M. Wilm, *Anal. Chem.* 66:4390-4399 (1994); J.A. Taylor and R.S. Johnson, *Rapid Comm. Mass Spec.* 11:1067-1075 (1997)). Searching programs that can be used in this process exist on the Internet, such as Lutefisk 97 (on the World Wide Web, at i-mass.com), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there also exists a need in the art for polypeptides suitable for use in peptide fragmentation studies, for use in molecular weight measurements, and for use in protein sequencing using tandem mass spectrometry.

SUMMARY OF THE INVENTION

The present invention provides isolated nucleic acids and polypeptides encoded by the nucleic acids for an IL-1 family ligand termed "IL-1 zeta" and three splice variants of IL-1 zeta, termed TDZ.1, TDZ.2, and TDZ.3. The present invention also provides isolated nucleic acid molecules and polypeptides encoded by the nucleic acid molecules for an IL-1 family receptor termed "Xrec2." Thus, in one aspect, the invention is directed to isolated nucleic acid molecules of IL-1 zeta, TDZ.1, TDZ.2, and TDZ.3 comprising the DNA sequence of SEQ ID NO:1, SEQ ID NO:5, SEQ ID NO:6, and SEQ ID NO:7, respectively, and nucleic acid molecules complementary to SEQ ID NO:1, 5, 6, and 7. Similarly, the invention is directed to isolated nucleic acid molecules of Xrec2 comprising the nucleic acid molecule of SEQ ID NO:2 and nucleic acid molecules complementary to SEQ ID NO:2. In another aspect, the invention is directed to isolated IL-1 zeta, TDZ.1, TDZ.2, and TDZ.3 polypeptides having the amino acid sequences SEQ ID NO:3 SEQ ID NO:8, SEQ ID NO:9, and SEQ ID NO:10, respectively, and nucleic acid molecules encoding the polypeptides of SEQ ID NO:3, 8, 9, and 10. Further included in the invention are isolated Xrec2 polypeptides comprising the amino acid sequence of SEQ ID NO:4 and nucleic acid molecules that encode the polypeptide of SEQ ID NO:4

Both single-stranded and double-stranded RNA and DNA nucleic acid molecules are encompassed by the invention, as well as nucleic acid molecules that hybridize to a denatured, double-stranded DNA comprising all or a portion of SEQ ID NOs:1, 2, 5, 6, and 7 and/or a DNA that encodes the amino acid sequences set forth in SEQ ID NOs:3, 4, 8, 9, and 10. Also encompassed are isolated nucleic acid molecules that are derived by in vitro mutagenesis of nucleic acid molecules comprising sequences of SEQ ID NOs:1, 2, 5, 6, and 7 that are degenerate from nucleic acid molecules comprising sequences of SEQ ID NOs:1, 2, 5, 6, and 7, and that are allelic variants of DNA of the invention. The invention also encompasses recombinant vectors that direct the expression of these nucleic acid molecules and host cells transformed or transfected with these vectors.

In addition, the invention encompasses methods of using the nucleic acids noted above to identify nucleic acids encoding proteins having activities associated with IL-1 family ligands and receptors. Thus, the IL-1 zeta nucleic acid molecules can be used to identify the IL-1 zeta receptor while the Xrec2 nucleic acid molecule can be used to identify the Xrec2 ligand.

In addition, these nucleic acids can be used to identify the human chromosomes with which the nucleic acids are associated. Thus, the IL-1 zeta, TDZ.1, TDZ.2, and TDZ.3 nucleic acids can be used to identify human chromosome 2 while the Xrec2 nucleic acids can be used to identify human chromosome X. Accordingly, these nucleic acids can also be used to map genes on human chromosomes 2 and X, respectively; to identify genes associated with certain diseases, syndromes, or other human conditions associated with human chromosomes 2 and X, respectively; and to study cell signal transduction and the immune system.

The invention also encompasses the use of sense or antisense oligonucleotides from the nucleic acids of SEQ ID NOs:1, 2, 5, 6, and 7 to inhibit the expression of the respective polynucleotide encoded by the genes of the invention.

The invention also encompasses isolated polypeptides and fragments of IL-1 zeta and Xrec2 as encoded by these nucleic acid molecules, including soluble polypeptide portions of SEQ ID NOs:3 4, 8, 9, and 10, respectively. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as immune regulation, cell proliferation, cell death, cell migration, cell-to-cell interaction, and inflammatory responses. In addition, these polypeptides can be used to identify proteins associated with IL-1 zeta, TDZ.1, TDZ.2, and TDZ.3 ligands and with Xrec2 receptors.

In addition, the invention includes assays utilizing these polypeptides to screen for potential inhibitors or enhancers of activity associated with the polypeptides of this invention. The present invention also includes assays and screening methods for identifying inhibitors or enhancers of activities associated with counter-structure molecules of the polypeptides of this invention. Further, methods of using these polypeptides in the design of inhibitors (e.g., engineered receptors that act as inhibitors) thereof are also an aspect of the invention.

The present invention further encompasses therapeutic methods utilizing antagonist and/or agonists of the polypeptides of this invention and antagonists or agonists discovered in accordance with the screening methods of this invention. For example, IL-1 zeta polypeptides of the present invention enhance the secretion of IL-12 from isolated primary human monocytes. In view of IL-12 activity associated with stimulating and enhancing immune responses and IL-12 activity in promoting Th1 mediated diseases, IL-1 zeta polypeptide agonists, together with IL-1 zeta antagonists are useful for treating disease or medical conditions associated with immune system imbalances, particularly imbalances involving cell-mediated immune responses. For example, inhibitors or antagonists of IL-1 zeta polypeptides can be used to treat disease associated with abnormal Th1 immune responses, including the deleterious effects of inflammation. Agonists of IL-1 zeta polypeptide activity are useful in treating disease responsive to IL-12 stimulation such as certain infectious diseases, including *Leishmania*, parasitic diseases and diseases preferentially inhibited by a Th1 immune response. Additionally Il-1 zeta polypeptides upregulate TNF expression and thus antagonists of IL-1 zeta polypeptides are useful in treating inflammatory conditions including rheumatoid arthritis, SLE, myasthenia gravis, insulin-dependent diabetes mellitus, thyroiditis, etc. and diseases preferentially inhibited by a Th1 immune response.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations.

Further encompassed by this invention is the use of the IL-1 zeta and Xrec2 nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition the use of these antibodies to aid in purifying the polypeptides of the invention.

DETAILED DESCRIPTION OF THE INVENTION

Figure 1:
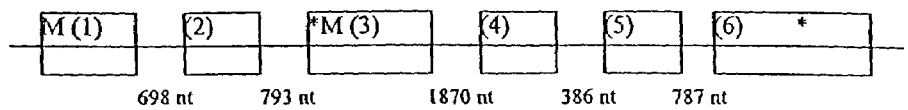
FIG. 1 diagrams the genomic structure of the IL-1 zeta locus.
Figure 1:
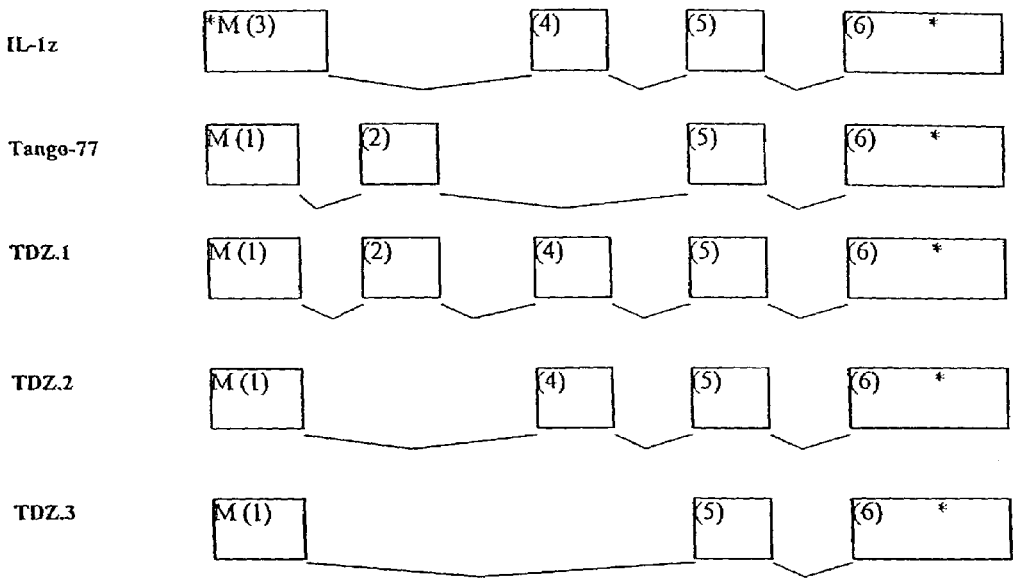

The nucleic acid molecules encompassed in the invention include the following nucleotide sequences:

```
Name: IL-1 zeta
                                                      (SEQ ID NO:1)
  1 ATGTCAGGCT GTGATAGGAG GGAAACAGAA ACCAAAGGAA AGAACAGCTT

51 TAAGAAGCGC TTAAGAGGTC CAAAGGTGAA GAACTTAAAC CCGAAGAAAT

101 TCAGCATTCA TGACCAGGAT CACAAAGTAC TGGTCCTGGA CTCTGGGAAT

151 CTCATAGCAG TTCCAGATAA AAACTACATA CGCCCAGAGA TCTTCTTTGC

201 ATTAGCCTCA TCCTTGAGCT CAGCCTCTGC GGAGAAAGGA AGTCCGATTC

251 TCCTGGGGGT CTCTAAAGGG GAGTTTTGTC TCTACTGTGA CAAGGATAAA

301 GGACAAAGTC ATCCATCCCT TCAGCTGAAG AAGGAGAAAC TGATGAAGCT

351 GGCTGCCCAA AAGGAATCAG CACGCCGGCC CTTCATCTTT TATAGGGCTC

401 AGGTGGGCTC CTGGAACATG CTGGAGTCGG CGGCTCACCC CGGATGGTTC

451 ATCTGCACCT CCTGCAATTG TAATGAGCCT GTTGGGGTGA CAGATAAATT

501 TGAGAACAGG AAACACATTG AATTTTCATT TCAACCAGTT TGCAAAGCTG

551 AAATGAGCCC CAGTGAGGTC AGCGATTAG
```

Name: Xrec2 (SEQ ID NO:2)

```
   1 ATGAAAGCTC CGATTCCACA CTTGATTCTC TTATACGCTA CTTTTACTCA
  51 GAGTTTGAAG GTTGTGACCA AAAGAGGCTC CGCCGATGGA TGCACTGACT
 101 GGTCTATCGA TATCAAGAAA TATCAAGTTT TGGTGGGAGA GCCTGTTCGA
 151 ATCAAATGTG CACTCTTTTA TGGTTATATC AGAACAAATT ACTCCCTTGC
 201 CCAAAGTGCT GGACTCAGTT TGATGTGGTA CAAAAGTTCT GGTCCTGGAG
 251 ACTTTGAAGA GCCAATAGCC TTTGACGGAA GTAGAATGAG CAAAGAAGAA
 301 GACTCCATTT GGTTCCGGCC AACATTGCTA CAGGACAGTG GTCTCTACGC
 351 CTGTGTCATC AGAAACTCCA CTTACTGTAT GAAAGTATCC ATCTCACTGA
 401 CAGTGGGTGA AAATGACACT GGACTCTGCT ATAATTCCAA GATGAAGTAT
 451 TTTGAAAAAG CTGAACTTAG CAAAAGCAAG GAAATTTCAT GCCGTGACAT
 501 AGAGGATTTT CTACTGCCAA CCAGAGAACC TGAAATCCTT TGGTACAAGG
 551 AATGCAGGAC AAAAACATGG AGGCCAAGTA TTGTATTCAA AAGAGATACT
 601 CTGCTTATAA GAGAAGTCAG AGAAGATGAC ATTGGAAATT ATACCTGTGA
 651 ATTAAAATAT GGAGGCTTTG TTGTGAGAAG AACTACTGAA TTAACTGTTA
 701 CAGCCCCTCT GACTGATAAG CCACCCAAGC TTTTGTATCC TATGGAAAGT
 751 AAACTGACAA TTCAGGAGAC CCAGCTGGGT GACTCTGCTA ATCTAACCTG
 801 CAGAGCTTTC TTTGGGTACA GCGGAGATGT CAGTCCTTTA ATTTACTGGA
 851 TGAAAGGAGA AAAATTTATT GAAGATCTGG ATGAAAATCG AGTTTGGGAA
 901 AGTGACATTA GAATTCTTAA GGAGCATCTT GGGGAACAGG AAGTTTCCAT
 951 CTCATTAATT GTGGACTCTG TGGAAGAAGG TGACTTGGGA AATTACTCCT
1001 GTTATGTTGA AATGGAAAT GGACGTCGAC ACGCCAGCGT TCTCCTTCAT
1051 AAACGAGAGC TAATGTACAC AGTGGAACTT GCTGGAGGCC TTGGTGCTAT
1101 ACTCTTGCTG CTTGTATGTT TGGTGACCAT CTACAAGTGT ACAAGATAG
1151 AAATCATGCT CTTCTACAGG AATCATTTTG GAGCTGAAGA GCTCGATGGA
1201 GACAATAAAG ATTATGATGC ATACTTATCA TACACCAAAG TGGATCCTGA
1251 CCAGTGGAAT CAAGAGACTG GGGAAGPAGA ACGTTTTGCC CTTGAAATCC
1301 TACCTGATAT GCTTGAAAAG CATTATGGAT ATAAGTTGTT TATACCAGAT
1351 AGAGATTTAA TCCCAACTGG AACATACATT GAAGATGTGG CAAGATGTGT
1401 AGATCAAAGC AAGCGGCTGA TTATTGTCAT GACCCCAAAT TACGTAGTTA
1451 GAAGGGGCTG GAGCATCTTT GAGCTGGAAA CCAGACTTCG AAATATGCTT
1501 GTGACTGGAG AAATTAAAGT GATTCTAATT GAATGCAGTG AACTGAGAGG
1551 AATTATGAAC TACCAGGAGG TGGAGGCCCT GAAGCACACC ATCAAGCTCC
1601 TGACGGTCAT TAAATGGCAT GGACCAAAAT GCAACAAGTT GAACTCCAAG
1651 TTCTGGAAAC GTTTACAGTA TGAAATGCCT TTTAAGAGGA TAGAACCCAT
1701 TACACATGAG CAGGCTTTAG ATGTCAGTGA GCAAGGGCCT TTTGGGGAGC
1751 TGCAGACTGT CTCGGCCATT TCCATGGCCG CGGCCACCTC CACAGCTCTA
1801 GCCACTGCCC ATCCAGATCT CCGTTCTACC TTTCACAACA CGTACCATTC
1851 ACAAATGCGT CAGAAACACT ACTACCGAAG CTATGAGTAC GACGTACCTC
1901 CTACCGGCAC CCTGCCTCTT ACCTCCATAG GCAATCAGCA TACCTACTGT
```

-continued
```
1951 AACATCCCTA TGACACTCAT CAACGGGCAG CGGCCACAGA CAAAATCGAG

2001 CAGGGAGCAG AATCCAGATG AGGCCCACAC AAACAGTGCC ATCCTGCCGC

2051 TGTTGCCAAG GGAGACCAGT ATATCCAGTG TGATATGGTG A
```

```
Name: TDZ.1
                                                      (SEQ ID NO:5)
  1 ATGTCCTTTG TGGGGAGAA CTCAGGAGTG AAAATGGGCT CTGAGGACTG

51 GGAAAAAGAT GAACCCCAGT GCTGCTTAGA AGACCCGGCT GTAAGCCCCC

101 TGGAACCAGG CCCAAGCCTC CCCACCATGA ATTTTGTTCA CACAAGTCCA

151 AAGGTGAAGA ACTTAAACCC GAAGAAATTC AGCATTCATG ACCAGGATCA

201 CAAAGTACTG GTCCTGGACT CTGGGAATCT CATAGCAGTT CCAGATAAAA

251 ACTACATACG CCCAGAGATC TTCTTTGCAT TAGCCTCATC CTTGAGCTCA

301 GCCTCTGCGG AGAAAGGAAG TCCGATTCTC CTGGGGGTCT CTAAAGGGGA

351 GTTTTGTCTC TACTGTGACA AGGATAAAGG ACAAAGTCAT CCATCCCTTC

401 AGCTGAAGAA GGAGAAACTG ATGAAGCTGG CTGCCCAAAA GGAATCAGCA

451 CGCCGGCCCT TCATCTTTTA TAGGGCTCAG GTGGGCTCCT GGAACATGCT

501 GGAGTCGGCG GCTCACCCCG GATGGTTCAT CTGCACCTCC TGCAATTGTA

551 ATGAGCCTGT TGGGGTGACA GATAAATTTG AGAACAGGAA ACACATTGAA

601 TTTTCATTTC AACCAGTTTG CAAAGCTGAA ATGAGCCCCA GTGAGGTCAG

651 CGATTAG
```

```
Name: TDZ.2
                                                      (SEQ ID NO:6)
  1 ATGTCCTTTG TGGGGGAGAA CTCAGGAGTG AAAATGGGCT CTGAGGACTG

51 GGAAAAAGAT GAACCCCAGT GCTGCTTAGA AGGTCCAAAG GTGAAGAACT

101 TAAACCCGAA GAAATTCAGC ATTCATGACC AGGATCACAA AGTACTGGTC

151 CTGGACTCTG GGAATCTCAT AGCAGTTCCA GATAAAAACT ACATACGCCC

201 AGAGATCTTC TTTGCATTAG CCTCATCCTT GAGCTCAGCC TCTGCGGAGA

251 AAGGAAGTCC GATTCTCCTG GGGTCTCTA AAGGGGAGTT TTGTCTCTAC

301 TGTGACAAGG ATAAAGGACA AAGTCATCCA TCCCTTCAGC TGAAGAAGGA

351 GAAACTGATG AAGCTGGCTG CCCAAAAGGA ATCAGCACGC CGGCCCTTCA

401 TCTTTTATAG GGCTCAGGTG GGCTCCTGGA ACATGCTGGA GTCGGCGGCT

451 CACCCCGGAT GGTTCATCTG CACCTCCTGC AATTGTAATG AGCCTGTTGG

501 GGTGACAGAT AAATTTGAGA ACAGGAAACA CATTGAATTT CATTTCAAC

551 CAGTTTGCAA AGCTGAAATG AGCCCCAGTG AGGTCAGCGA TTAG
```

```
Name: TDZ.3
                                                      (SEQ ID NO:7)
  1 ATGTCCTTTG TGGGGAGAA CTCAGGAGTG AAAATGGGCT CTGAGGACTG

51 GGAAAAAGAT GAACCCCAGT GCTGCTTAGA AGAGATCTTC TTTGCATTAG

101 CCTCATCCTT GAGCTCAGCC TCTGCGGAGA AAGGAAGTCC GATTCTCCTG

151 GGGTCTCTA AAGGGGAGTT TTGTCTCTAC TGTGACAAGG ATAAAGGACA

201 AAGTCATCCA TCCCTTCAGC TGAAGAAGGA GAAACTGATG AAGCTGGCTG
```

```
-continued
251 CCCAAAAGGA ATCAGCACGC CGGCCCTTCA TCTTTTATAG GGCTCAGGTG

301 GGCTCCTGGA ACATGCTGGA GTCGGCGGCT CACCCCGGAT GGTTCATCTG

351 CACCTCCTGC AATTGTAATG AGCCTGTTGG GGTGACAGAT AAATTTGAGA

401 ACAGGAAACA CATTGAATTT TCATTTCAAC CAGTTTGCAA AGCTGAAATG

451 AGCCCCAGTG AGGTCAGCGA TTAG
```

The amino acid sequences of the polypeptides encoded by the nucleotide sequence of the invention include:

```
Name: IL-1 zeta (polypeptide)
                                                     (SEQ ID NO:3)
  1 MSGCDRRETE TKGKNSFKKR LRGPKVKNLN PKKFSIHDQD HKVLVLDSGN

51 LIAVPDKNYI RPEIFFALAS SLSSASAEKG SPILLGVSKG EFCLYCDKDK

101 GQSHPSLQLK KEKLMKLAAQ KESARRPFIF YRAQVGSWNM LESAAHPGWF

151 ICTSCNCNEP VGVTDKFENR KHIEFSFQPV CKAEMSPSEV SD*

Name: Xrec2 (polypeptide)
                                                     (SEQ ID NO:4)
  1 MKAPIPHLIL LYATFTQSLK VVTKRGSADG CTDWSIDIKK YQVLVGEPVR

51 IKCALFYGYI RTNYSLAQSA GLSLMWYKSS GPGDFEEPIA FDGSRMSKEE

101 DSIWFRPTLL QDSGLYACVI RNSTYCMKVS ISLTVGENDT GLCYNSKMKY

151 FEKAELSKSK EISCRDIEDF LLPTREPEIL WYKECRTKTW RPSIVFKRDT

201 LLIREVREDD IGNYTCELKY GGFVVRRTTE LTVTAPLTDK PPKLLYPMES

251 KLTIQETQLG DSANLTCRAF FGYSGDVSPL IYWMKGEKFI EDLDENRVWE

301 SDIRILKEHL GEQEVSISLI VDSVEEGDLG NYSCYVENGN GRRHASVLLH

351 KRELMYTVEL AGGLGAILLL LVCLVTIYKC YKIEIMLFYR NHFGAEELDG

401 DNKDYDAYLS YTKVDPDQWN QETGEEERFA LEILPDMLEK HYGYKLFIPD

451 RDLIPTGTYI EDVARCVDQS KRLIIVMTPN YVVRRGWSIF ELETRLRNML

501 VTGEIKVILI ECSELRGIMN YQEVEALKHT IKLLTVIKWH GPKCNKLNSK

551 FWKRLQYEMP FKRIEPITHE QALDVSEQGP FGELQTVSAI SMAAATSTAL

601 ATAHPDLRST FHNTYHSQMR QKHYYRSYEY DVPPTGTLPL TSIGNQHTYC

651 NIPMTLTNGQ RPQTKSSREQ NPDEAHTNSA ILPLLPRETS ISSVIW*

TDZ.1 polypeptide
                                                     (SEQ ID NO:8)
  1 MSFVGENSGV KMGSEDWEKD EPQCCLEDPA VSPLEPGPSL PTMNFVHTSP

51 KVKNLNPKKF SIHDQDHKVL VLDSGNLIAV PDKNYIRPEI FFALASSLSS

101 ASAEKGSPIL LGVSKGEFCL YCDKDKGQSH PSLQLKKEKL MKLAAQKESA

151 RRPFIFYRAQ VGSWNMLESA AHPGWFICTS CNCNEPVGVT DKFENRKHIE

201 FSFQPVCKAE MSPSEVSD*
```

```
Name: TDZ.2 polypeptide
                                                       (SEQ ID NO:9)
  1 MSFVGENSGV KMGSEDWEKD EPQCCLEGPK VKNLNPKKFS IHDQDHKVLV
 51 LDSGNLIAVP DKNYIRPEIF FALASSLSSA SAEKGSPILL GVSKGEFCLY

101 CDKDKGQSHP SLQLKKEKLM KLAAQKESAR RPFIFYRAQV GSWNMLESAA

151 HPGWFICTSC NCNEPVGVTD KFENRKHIEF SFQPVCKAEM SPSEVSD*

Name: TDZ.3 polypeptide
                                                       (SEQ ID NO:10)
  1 MSFVGENSGV KMGSEDWEKD EPQCCLEEIF FALASSLSSA SAEKGSPILL

51 GVSKGEFCLY CDKDKGQSHP SLQLKKEKLM KLAAQKESAR RPFIFYRAQV

101 GSWNMLESAA HPGWFICTSC NCNEPVGVTD KFENRKHIEF SFQPVCKAEM

151 SPSEVSD*
```

The discovery of the IL-1 zeta, the IL-1 zeta splice variants (TDZ.1, TDZ.2, and TDZ.3) and the Xrec2 nucleic acids of the invention enables the construction of expression vectors comprising nucleic acid sequences encoding the respective polypeptides and host cells transfected or transformed with the expression vectors. The invention also enables the isolation and purification of biologically active IL-1 zeta, the IL-1 zeta splice variants, and Xrec2 polypeptides and fragments thereof. In yet another embodiment, the nucleic acids or oligonucleotides thereof can be used as probes to identify nucleic acid encoding proteins having associated activities. Thus, IL-1 zeta and the IL-1 splice variants can be used to identify activities associated with IL-1 family ligands and Xrec2 can be used to identify activities associated with IL-1 family receptors. In addition, the nucleic acids or oligonucleotides thereof of IL-1 zeta can be used to identify human chromosomes 2 while those of Xrec2 can be used to identify human chromosome X. Similarly, these nucleic acids or oligonucleotides thereof can be used to map genes on human chromosomes 2 and X, respectively, and to identify genes associated with certain diseases, syndromes or other human conditions associated with human chromosomes 2 and X. Thus, the nucleic acids or oligonucleotides thereof of IL-1 zeta, TDZ.1, TDZ.2, and TDZ.3 can be used to identify glaucoma, ectodermal dysplasia, insulin-dependent diabetes mellitus, wrinkly skin syndrome, T-cell leukemia/lymphoma, and tibial muscular dystrophy while the nucleic acids or oligonucleotides thereof of Xrec2 can be used to identify retinoschisis, lissencephaly, subcortical laminalheteropia, mental retardation, cowchock syndrome, bazex syndrome, hypertrichosis, lymphoproliferative syndrome, immunodeficiency, Langer mesomelic dysplasia, and leukemia. Finally, single-stranded sense or antisense oligonucleotides from these nucleic acids can be used to inhibit expression of polynucleotides encoded by the IL-1 zeta and Xrec2 genes, respectively.

Further, the IL-1 zeta, TDZ.1, TDZ.2, TDZ.3 and Xrec2 polypeptides and soluble fragments thereof can be used to activate and/or inhibit the activation of vascular endothelial cells and lymphocytes, induce and/or inhibit the induction of local tissue destruction and fever (Janeway et al., 1996), inhibit and/or stimulate macrophages and vascular endothelial cells to produce IL-6, induce and/or inhibit the induction of prostaglandins, nitric oxide synthetase, and metalloproteinases, and upregulate and/or inhibit the upregulation of molecules on the surface of vascular endothelial cells. In addition these polypeptides and fragmented peptides can also be used to induce and/or inhibit the induction of inflammatory mediators such as transcription factors NF-κB and AP-1, MAP kinases JNK and p38, COX-2, iNOS, and all of the activities stimulated by these molecules.

In addition, these polypeptides and fragmented peptides can be used as molecular weight markers and as controls for peptide fragmentation, and the invention includes the kits comprising these reagents. Finally, these polypeptides and fragments thereof can be used to generate antibodies, and the invention includes the use of such antibodies to purify IL-1 zeta and Xrec2 polypeptides.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NOs:1, 2, 5, 6, 7 or a suitable fragment thereof, as a probe.

The DNA molecules of the invention include full length genes as well as polynucleotides and fragments thereof. The full length gene may include the N-terminal signal peptide. Other embodiments include DNA encoding a soluble form, e.g., encoding the extracellular domain of the protein, either with or without the signal peptide.

The nucleic acids of the invention are preferentially derived from human sources, but the invention includes those derived from non-human species, as well.

Preferred Sequences

The particularly preferred nucleic acid molecules of the invention are those shown in SEQ ID NOs:1, 5, 6, 7 for IL-1 zeta, TDZ.1, TDZ.2, and TDZ.3, respectively, and SEQ ID NO:2 for Xrec2. cDNA clones having the nucleic acid sequence of SEQ ID NOs:1 and 2 were isolated as described in Example 1. The sequences of the amino acids of IL-1 zeta and Xrec2 encoded by the DNAs of SEQ ID NOs:1 and 2 are shown in SEQ ID NOs:3 and 4, respectively. CDNA clones having the nucleic acid sequence of SEQ ID NOs:5, 6, and 7 were isolated as described in Example 8. The sequences of the amino acids of TDZ.1, TDZ.2, and TDZ.3 encoded by the DNAs of SEQ ID NOs:5, 6, and 7 are shown in SEQ ID NOs:8, 9, and 10, respectively.

SEQ ID NOs:1-4 identify the IL-1 zeta of SEQ ID NO:3 as a member of the IL-1 family and the Xrec2 of SEQ ID NO:4 as a member of the IL-1 receptor family. The homologies on which this is based is set forth at Table I below:

TABLE I

| Protein | Source | Percent identity to IL-1 zeta |
|---|---|---|
| IL-1 alpha | Human | LOW |
| IL-1 beta | Human | 22% |
| IL-1 delta | Human | 34% |
| IL-1 epsilon | Human | 34% |
| IL-18 | Human | LOW |
| IL-1ra | Human | 29% |

| Protein | Source | Percent identity to Xrec2 |
|---|---|---|
| TIGIRR (IL-1R family member) | Human | 63% |
| TIGIRR (IL-1R family member) | Murine | 61% |
| SIGIRR | Human | 22% |
| IL-1R-AcP | Human | 35% |
| IL-1R-AcPL | Human | 26% |
| IL-1R | Human | 29% |
| RP1 | Human | 31% |
| RP2 | Human | 28% |
| ST2 | Human | 26% |

Percent identity of IL-1 zeta and Xrec2 to human and murine proteins.

As described in Example 8, the IL-1 zeta splice variants were discovered in a stretch of genomic DNA sequence (X22304.gbn). This genomic sequence also contains the different IL-1 zeta exons and another splice variant known as Tango-77 (WO 99/06426). Comparing the cDNA sequences of the cloned IL-1 zeta, TDZ.1, TDZ.2, TDZ.3 and Tango-77 with the genomic sequence provides insight into the generation of the splicing events. FIG. 1 shows the genomic structure of the IL-1 zeta locus and the cDNA generated by alternative splicing. The numbered boxes indicate individual exons 1-6 and the approximate size of the intervening introns is indicated at the top. The asterisk (*) indicates the presence of a stop codon, at the end of the coding sequence (exon 6) or as an in-frame stop codon (exon 3). "M" indicates potential initiating methionine originating either from exon 1 or exon 3. Tango-77 is the cDNA structure disclosed in WO 99/06426. A significant feature of IL-1 zeta and its splice variants is the presence or absence of exon 4. Exon 4 is present in IL-1 zeta, TDZ.1 and TDZ.2. It is not present in Tango-77. The amino acid sequence encoded by exon 4 aligns well with the amino acid sequences of other IL-1 family members in the first few beta strands of the mature peptides. By contrast, the amino acid sequence encoded by Tango-77 cDNA and by TDZ.3 cDNA aligns well with other IL-1 family members in the regions encoded by exons 5 and 6. Exons 5 and 6 align well with amino acid sequences of other IL-1 family members in the C-terminal 2/3 of the mature peptide, but does not align well in the N-terminal 1/3. Thus, the "mature peptide" encoded by IL1zeta, TDZ.1 and TDZ.2 DNAs is likely to represent a functional IL-1 like molecule. This contrasts with the polypeptide encoded by Tango-77 or TDZ.3 DNAS which are less likely to represent a functional IL-1 like molecule.

It is probable that all of the splice isoforms, except TDZ.3, encode proforms of an IL-1 like cytokine, since in the N-terminal direction the DNAs extend well beyond the N-terminus of mature IL-1s. This observation predicts that IL-1zeta, TDZ.1 and TDZ.2 encode the same mature peptide. In connection with this observation it is the pro-domains (as well as 5' UTRs) that differs between IL-1 zeta, TDZ.1 and TDZ.2.

Table II, which details the tissue distribution of IL-1 zeta, TDZ.1, TDZ.2, TDZ.3 and Tango-77, shows that the expression of Tango-77 is more widespread than that of IL-1 zeta. Table II also shows that the TDZ.1 expression is comparable, and almost entirely overlapping, with that of Tango-77. The tissue distribution data combined with the alignment information of FIG. 1 shows that TDZ.1 is the only member of the splice variants that aligns well with other IL-1 family members, and is widespread in its expression. These observations suggest that TDZ.1 may be the most significant of the splice variants in terms of group in terms of relevance to biological responses.

Additional Sequences

Due to the known degeneracy of the genetic code, wherein more than one codon can encode the same amino acid, a DNA sequence can vary from that shown in SEQ ID NOs:1, 2, 5, 6, and 7 and still encode a polypeptide having the amino acid sequence of SEQ ID NOs:3, 4, 8, 9, and 10, respectively. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequences of SEQ ID NOs:1, 2; 5, 6, and 7 (b) DNA encoding the polypeptides of SEQ ID NOs:3, 4; 8, 9, and 10 (c) DNA capable of hybridization to a DNA of (a) or (b) under conditions of moderate. stringency and which encodes polypeptides of the invention; (d) DNA capable of hybridization to a DNA of (a) or (b) under conditions of high stringency and which encodes polypeptides of the invention, and (e) DNA which is degenerate, as a result of the genetic code, to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al. *Molecular Cloning: A Laboratory Manual,* 2 ed. Vol. 1, pp. 1.101-104, Cold Spring Harbor Laboratory Press, (1989), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2× SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution(s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The invention provides isolated nucleic acids useful in the production of polypeptides. Such polypeptides may be prepared by any of a number of conventional techniques. A DNA sequence encoding a polypeptide of the invention, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et al., eds., Academic Press, Inc. (1990).

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

The polypeptides of the invention include full length proteins encoded by the nucleic acid sequences set forth above. Particularly preferred polypeptides of IL-1 zeta, TDZ.1, TDZ.2 TDZ.3 and Xrec2 comprise the amino acid sequence of SEQ ID NOs:3, 4, 8, 9, and 10 respectively. For TDZ.1 and TDZ.2 the N-terminus does not encode a classical signal peptide but the extra length relative to the mature form other family members is suggestive that it may act as a prodomain. A predicted cleavage site is the point where the conserved structural portion of the protein begins. Structural modeling data supports this assumption. For IL-1 zeta and the TDZ.1 and TDZ.2 variants site is somewhere immediately upstream of the last three exons. Thus, the polypeptide of IL-1 zeta, as set forth in SEQ ID NO:3, includes a putative pro-domain that extends from amino acids 1 to x, where x is an integer from 20 to 50. Similarly, TDZ.1 of SEQ ID NO:8 includes a putative prodomain that extends from amino acids 1 to x' where x' is an integer from 40-50 and most preferably x' is about 48. TDZ.2 of SEQ ID NO:9 includes a putative prodomain that extends from amino acids 1 to x", where x" is an integer from 25-30 and most preferable x" is 27.

Unlike IL-1 zeta and its splice variants, the polypeptide of Xrec2, as set forth in SEQ ID NO:4, includes an N-terminal hydrophobic region that functions as a signal peptide, followed by an extracellular domain comprising amino acids 19 to 359, a transmembrane region comprising amino acids 360 through 378, and a C-terminal cytoplasmic domain comprising amino acids 379 to 696. Computer analysis predicts that the signal peptide corresponds to residues 1 to 19 of SEQ ID NO:4 (although the next most likely computer-predicted signal peptide cleavage sites (in descending order) occur after amino acids 20 and 16 of SEQ ID NO:4.)). Cleavage of the signal peptide thus would yield a mature protein comprising amino acids 19 through 696 of SEQ ID NO:4.

The skilled artisan will recognize that the above-described boundaries of such regions of the polypeptide are approximate. To illustrate, the boundaries of the transmembrane region (which may be predicted by using computer programs available for that purpose) may differ from those described above.

The polypeptides of the invention may be membrane bound or they may be secreted and, thus, soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may include the cytoplasmic domain, or a portion thereof, as long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Particular embodiments are directed to polypeptide fragments of SEQ ID NOs:3, 4, 8, 9, and 10 that retain the ability to bind the native cognates, substrates, or counter-structure ("binding partner"). Such a fragment may be a soluble polypeptide, as described above. In another embodiment, the polypeptides and fragments advantageously include regions that are conserved in the IL-1 ligand and IL-1 receptor family as described above.

Also provided herein are polypeptide fragments comprising at least 20, or at least 30, contiguous amino acids of the sequences of SEQ ID NOs:3 4, 8, 9, and 10. In one aspect, fragments derived from the cytoplasmic domain of Xrec2 of SEQ ID NO:4 find use in studies of signal transduction, and in regulating cellular processes associated with transduction of biological signals. Polypeptide fragments also may be employed as immunogens, in generating antibodies.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG[7] peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG[7] peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG[7] peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain IL-1 zeta, TDZ.1, TDZ.2, TDZ.3 or Xrec2 polypeptides. When the polypeptide of the invention is a type I membrane protein, such as Xrec2, the fusion partner is linked to the C terminus of the type I membrane protein. Such oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151, hereby incorporated by reference, is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four polypeptide extracellular regions.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble polypeptides of the invention, separated by peptide linkers.

Leucine-Zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins,fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form heterodimers (O'Shea et al., *Science* 245:646, 1989, Turner and Tjian, *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland and Wild, *Nature* 338:547,1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259:230, 1993).

Zipper domains fold as short, parallel coiled coils. (O'Shea et al., *Science* 254:539; 1991) The general architecture of the parallel coiled coil has been well characterized, with a "knobs-into-holes" packing as proposed by Crick in 1953 (*Acta Crystallogr.* 6:689). The dimer formed by a zipper domain is stabilized by the heptad repeat, designated (abcdefg)$_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al. (*Science* 262:1401, 26 Nov. 1993)

Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD), as described in Hoppe et al. (*FEBS Letters* 344:191, 1994) and in U.S. Pat. No. 5,716,805, hereby incorporated by reference in their entirety. This lung SPD-derived leucine zipper peptide comprises the amino acid sequence Pro Asp Val Ala Ser Leu Arg Gln Val Glu Ala Leu Gln Gly Gln Val Gln His Leu Gln Ala Phe Ser Gln Tyr.

Another example of a leucine zipper that promotes trimerization is a peptide comprising the amino acid sequence Arg Met Lys Gln Ile Glu Asp Lys Ile Glu Ile Leu Ser Lys Ile Tyr His Ile Glu Asn Glu Ile Ala Arg Ile Lys Leu Ile Gly Glu Arg, as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric oligomers. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site. Particular embodiments of mature proteins provided herein include, but are not limited to, proteins having the residue at position 6, 23, 25, 26, 39, 41, or 48 of SEQ ID NO:3 and at position 1 or 19 of SEQ ID NO:4 as the N-terminal amino acid.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, New York, (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* ($Amp^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture,* 1990, pp. 15-69). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual,* 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology,* 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology,* 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology,* 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology,* 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Another useful expression vector, pFLAG$^7$, can be used. FLAG$^7$ technology is centered on the fusion of a low molecular weight (1 kD), hydrophilic, FLAG$^7$ marker peptide to the N-terminus of a recombinant protein expressed by pFLAG$^7$ expression vectors.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reverse-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means. For example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. *J. Cell. Biochem.*, 10D:239 (1986). Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind the binding partner in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing the binding partner. The cells then are washed to remove unbound labeled polypeptide, and the presence of cell-bound label is determined by a suitable technique, chosen according to the nature of the label.

One example of a binding assay procedure is as follows. A recombinant expression vector containing the binding partner cDNA is constructed using methods well known in the art. CV1-EBNA-1 cells in 10 cm$^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about $4\times10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, a soluble polypeptide/Fc fusion protein made as set forth above. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a variant may be determined by assaying for the variant's ability to compete with the native protein for binding to the binding partner.

Competitive binding assays can be performed by conventional methodology. Reagents that may be employed in competitive binding assays include radiolabeled polypeptides of the invention and intact cells expressing the binding partner (endogenous or recombinant). For example, a radiolabeled soluble IL-1 zeta fragment can be used to compete with a soluble IL-1 zeta variant for binding to cell surface IL-1 zeta receptors. Instead of intact cells, one could substitute a soluble binding partner/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble binding partner, such as a soluble IL-1 zeta receptor/Fc fusion or Xrec2 ligand/Fc fusion protein, and intact cells expressing the binding partner. Qualitative results can be obtained by competitive autoradiographic plate binding assays, while Scatchard plots (Scatchard, *Ann. N.Y. Acad. Sci.* 51:660, 1949) may be utilized to generate quantitative results.

Use of IL-1 Zeta, TDZ.1, TDZ.2, TDZ.3 and Xrex2 Nucleic Acid or Oligonucleotides In addition to being used to express polypeptides as described above, the nucleic acids of the invention, including DNA, and oligonucleotides thereof can be used:
- as probes to identify nucleic acid encoding proteins of the IL-1 ligand and receptor families;
- to identify human chromosomes 2 and X;
- to map genes on human chromosomes 2 and X;
- to identify genes associated with certain diseases, syndromes, or other conditions associated with human chromosomes 2 and X;
- as single-stranded sense or antisense oligonucleotides, to inhibit expression of polypeptides encoded by the IL-1 zeta, TDZ.1, TDZ.2, TDZ.3 and Xrec2 genes;
- to help detect defective genes in an individual; and
- for gene therapy.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NOs:1, 2, 5, 6 and 7, from other mammalian species, are contemplated herein, probes based on the human DNA sequences of SEQ ID NOs: 1, 2, 5, 6 and 7 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

All or a portion of the nucleic acids of IL-1 zeta of SEQ ID NO:1 and of Xrec2 of SEQ ID NO:2, including oligonucleotides, can be used by those skilled in the art using well-known techniques to identify the human chromosomes 2 and X, respectively, as well as the specific locus thereof, that contains the DNA of IL-1 ligand and IL-1 receptor family members. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybridization. PCR is performed using the Whitehead Institute/MIT Center for Genome Research Genebridge4 panel of 93 radiation hybrids (http://www-genome.wi.mit.edu/ftp/distribution/human_STS_releases/july97/rhmap/genebridge4.html). Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (http://www-seq.wi.mit.edu). The data is scored and the chromosomal assignment and placement relative to known Sequence Tag Site (STS) markers on the radiation hybrid map is provided. The following web site provides additional information about radiation hybrid mapping: http://www-genome.wi.mit.edu/ftp/distribution/human_STS_releases/july97/07-97.INTRO.html).

Identifying Associated Diseases

As set forth below, IL-1 zeta of SEQ ID NO:1, IL-1 zeta splice variants, and Xrec2 of SEQ ID NO:2 have been mapped by radiation hybridization and high-throughput-shotgun sequencing to the 2q11-12 and Xp22 regions of human chromosomes 2 and X, respectively. Human chromosome 2 is associated with specific diseases which include but are not limited to glaucoma, ectodermal dysplasia, insulin-dependent diabetes mellitus, wrinkly skin syndrome, T-cell leukemia/lymphoma, and tibial muscular dystrophy while human chromosome X is associated with retinoschisis, lissencephaly, subcortical laminalheteropia, mental retardation, cowchock syndrome, bazex syndrome, hypertrichosis, lymphoproliferative syndrome, immunodeficiency, Langer mesomelic dysplasia, and leukemia. Thus, the nucleic acids of SEQ ID NOs:1 and 2 or a fragment thereof can be used by one skilled in the art using well-known techniques to analyze abnormalities associated with gene mapping to chromosomes 2 and X. This enables one to distinguish conditions in which this marker is rearranged or deleted. In addition, nucleotides of SEQ ID NOs: 1, 2, 5, 6 and 7 or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides according to the present invention comprise a fragment of DNA (SEQ ID NOs: 1, 2, 5, 6 and 7). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, CaPO$_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

IL-1 zeta anti-sense are useful as therapeutics to treat medical conditions and disease associated with immune system dysfunction and IL-12 production. Such medical conditions and disease are described below and include the deleterious effects of inflammation and auto-immune diseases. Accordingly, IL-1 zeta anti-sense are IL-12 antagonists and are useful in treating disease and medical conditions that are benefited by IL-12 expression downregulation.

Use of IL-1 Zeta TDZ.1, TDZ.2 TDZ.3 and Xrec2 Polypeptides and Fragmented Polypeptides Uses include, but are not limited to, the following:
Purifying proteins and measuring activity thereof
Delivery Agents
Therapeutic and Research Reagents
Molecular weight and Isoelectric focusing markers
Controls for peptide fragmentation
Identification of unknown proteins
Preparation of Antibodies
Purification Reagents Each of the polypeptides of the invention finds use as a protein purification reagent. The polypeptides may be attached to a solid support material and used to purify the binding partner proteins by affinity chromatography. In particular embodiments, a polypeptide (in any form described herein that is capable of binding the binding partner) is attached to a solid support by conventional procedures. As one example, chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express the binding partner on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing the binding partner expressing cells are contacted with the solid phase having the polypeptides thereon. Cells expressing the binding partner on the cell surface bind to the fixed polypeptides, and unbound cells then are washed away.

Alternatively, the polypeptides can be conjugated to a detectable moiety, then incubated with cells to be tested for binding partner expression. After incubation, unbound labeled matter is removed and the presence or absence of the detectable moiety on the cells is determined.

In a further alternative, mixtures of cells suspected of containing cells expressing the binding partner are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.,* 10D:239, 1986). Washing to remove unbound material, and the release of the bound cells, are performed using conventional methods.

Measuring Activity

Polypeptides also find use in measuring the biological activity of the binding partner protein in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of a binding partner protein that has been stored at different temperatures, or produced in different cell types. The proteins also may be used to determine whether biological activity is retained after modification of a binding partner protein (e.g., chemical modification, truncation, mutation, etc.). The binding affinity of the modified binding partner protein is compared to that of an unmodified binding partner protein to detect any adverse impact of the modifications on biological activity of the binding partner. The biological activity of a binding partner protein thus can be ascertained before it is used in a research study, for example.

Delivery Agents

The polypeptides also find use as carriers for delivering agents attached thereto to cells bearing the binding partner. The polypeptides thus can be used to deliver diagnostic or therapeutic agents to such cells (or to other cell types found to express the binding partner on the cell surface) in in vitro or in vivo procedures.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Therapeutic Agents

Polypeptides of the invention may be used in developing treatments for any disorder mediated (directly or indirectly) by defective, or insufficient amounts of the polypeptides. These polypeptides may be administered to a mammal afflicted with such a disorder.

The polypeptides may also be employed in inhibiting a biological activity of the binding partner, in in vitro or in vivo procedures. For example, a purified Xrec2 receptor polypeptide may be used to inhibit binding of Xrec2 ligand to endogenous cell surface Xrec2 receptor, or a purified IL-1 zeta polypeptide, or any of its splice variants can be used to inhibit binding of endogenous IL-1 zeta or splice variants to its cell surface receptor. Biological effects that result from the binding of Xrec2 ligand to endogenous Xrec2 receptors thus are inhibited. In particular, IL-1 zeta polypeptides and fragments of these polypeptides that induce IL-12 expression are useful to upregulate IL-12 expression in individuals who can benefit from increased IL-12 production, including individuals who benefit from enhanced cell mediated immunity. Diseases and medical conditions treatable with agonists of IL-1 zeta polypeptide, as described below, may be suitably treated using IL-1 zeta polypeptides and fragments of this invention.

Polypeptides of the invention may be administered to a mammal to treat a binding partner-mediated disorder. Such binding partner-mediated disorders include conditions caused (directly or indirectly) or exacerbated by the binding partner.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble polypeptides of the invention.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Research Agents

Another use of the polypeptide of the present invention is as a research tool for studying the biological effects that result from the interactions of IL-1 zeta, or any of its splice variants, with its binding partner, and of Xrec2 with its binding partner, or from inhibiting these interactions, on different cell types. Polypeptides also may be employed in in vitro assays for detecting IL-1 zeta, Xrec2, the respective binding partners or the interactions thereof.

Another embodiment of the invention relates to uses of the polypeptides of the invention to study cell signal transduction. IL-1 family ligands and receptors play a central role in protection against infection and immune inflammatory responses which includes cellular signal transduction, activating vascular endothelial cells and lymphocytes, induction of inflammatory cytokines, acute phase proteins, hematopoiesis, fever, bone resorption, prostaglandins, metalloproteinases, and adhesion molecules. With the continued increase in the number of known IL-1 family members, a suitable classification scheme is one based on comparing polypeptide structure as well as function (activation and regulatory properties). Thus, IL-1 zeta, TDZ.1, TDZ.2, and TDZ.3, like other IL-1 family ligands (IL-1α, IL-1β, and IL-18) and Xrec2, like other IL-1R family receptors (IL-1RI, IL-1RII, IL-1Rrp1, and AcPL), would likely be involved in many of the functions noted above as well as promote inflammatory responses and therefore perhaps be involved in the causation and maintenance of inflammatory and/or autoimmune diseases such as rheumatoid arthritis, inflammatory bowel disease, and psoriasis. As such, alterations in the expression and/or activation of the polypeptides of the invention can have profound effects on a plethora of cellular processes, including, but not limited to, activation or inhibition of cell specific responses and proliferation. Expression of cloned IL-1 zeta, Xrec2, or of functionally inactive mutants thereof can be used to identify the role a particular protein plays in mediating specific signaling events.

IL-1 mediated cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adapter molecules that facilitate down stream signaling through protein-protein interaction following phosphorylation. Regardless of the nature of the substrate molecule(s), expressed functionally active versions of Xrec2, IL-1 zeta, its splice variants, and their binding partners can be used to identify what substrate(s) were recognized and activated by the polypeptides of the invention. As such, these novel polypeptides can be used as reagents to identify novel molecules involved in signal transduction pathways.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238-255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44-50, 1981; T. Masaki et al., *Biochim. Biophys. Acta* 660:51-55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102-1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

The polypeptides and the resultant fragmented peptides can be analyzed by methods including sedimentation, electrophoresis, chromatography, and mass spectrometry to determine their molecular weights. Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680-685, 1970). Conventionally, the method uses two separate lanes of a gel containing sodium dodecyl sulfate and a concentration of acrylamide between 6-20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76-77 (Prentice Hall, 6d ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252: 1102-1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the IL-1 zeta polypeptide of SEQ ID NO:3 with cyanogen bromide generates a unique set of fragmented peptide molecular weight markers with molecular weights of approximately 701.7, 2955.4, 5101.8 and 12688.5 Daltons. Additionally, fragmentation of the Xrec2 polypeptide of SEQ ID NO:4 with cyanogen bromide generates the following fragmented peptide molecular weight markers with molecular weights of approximately 2216.7, 2259.6, 2376.6, 2738.1, 2901.1, 3417.2, 3627.1, 3656.1, 4042.5, 4144.6, 4668.1, 4710.5, 4916.8, 5288.1, 6089.5, 8199.1, and 11919.7 Daltons in the absence of glycosylation. In the fragmentation of both SEQ ID NOs:3 and 4, an additional fragment of 149.2 Daltons results if the initiating methionine is present. The distribution of methionine residues determines the number of amino acids in each peptide and the unique amino acid composition of each peptide determines its molecular weight.

In addition, the preferred purified polypeptides of the invention (SEQ ID NOs:3 and 4) have a calculated molecular weight of approximately 21542.56 and 79967.85 Daltons, respectively. Thus, where an intact protein is used, the use of these polypeptide molecular weight markers allows increased accuracy in the determination of apparent molecular weight of proteins that have apparent molecular weights close to 21542.56 and 79967.85 Daltons. Where fragments are used, there is increased accuracy in determining molecular weight over the range of the molecular weights of the fragment.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., Proc. Natl. Acad. Sci. USA 90:5011-5015, 1993; D. Fenyo et al., Electrophoresis 19:998-1005, 1998). A variety of computer software programs to facilitate these comparisons are accessible via the Internet, such as Protein Prospector (Internet site: prospector.uscf.edu), MultiIdent (Internet site: www.expasy.ch/sprot/multiident.html), PeptideSearch (Internet site:www.mann.embl-heiedelberg.de...deSearch/FR_PeptideSearch Form.html), and ProFound (Internet site:www.chait-sgi.rockefeller.edu/cgi-bin/prot-id-frag.html). These programs allow the user to specify the cleavage agent and the molecular weights of the fragmented peptides within a designated tolerance. The programs compare observed molecular weights to predicted peptide molecular weights derived from sequence databases to assist in determining the identity of the unknown protein.

In addition, a polypeptide or peptide digest can be sequenced using tandem mass spectrometry (MS/MS) and the resulting sequence searched against databases (J. K. Eng, et al., J. Am. Soc. Mass Spec. 5:976-989 (1994); M. Mann and M. Wilm, Anal. Chem. 66:4390-4399 (1994); J. A. Taylor and R. S. Johnson, Rapid Comm. Mass Spec.11:1067-1075 (1997)). Searching programs that can be used in this process exist on the Internet, such as Lutefisk 97 (Internet site: www.lsbc.com:70/Lutefisk97.html), and the Protein Prospector, Peptide Search and ProFound programs described above.

Therefore, adding the sequence of a gene and its predicted protein sequence and peptide fragments to a sequence database can aid in the identification of unknown proteins using mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens" in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography. Those antibodies that additionally can block binding of the polypeptides of the invention to the binding partner may be used to inhibit a biological activity that results from such binding. Such blocking antibodies may be identified using any suitable assay procedure, such as by testing antibodies for the ability to inhibit binding of IL-1 zeta to certain cells expressing the IL-1 zeta receptors. Alternatively, blocking antibodies may be identified in assays for the ability to inhibit a biological effect that results from polypeptides of the invention binding to their binding partners to target cells. Antibodies may be assayed for the ability to inhibit IL-1 zeta-mediated, Xrec2-mediated, or binding partner-mediated cell lysis, for example. Antibodies that are antagonistic or block IL-1 zeta activity are useful as therapeutic agents for downregulating IL-12 expression and TNF expression. Thus, such antagonists are useful in treating deleterious affects of inflammation and disease associated with adverse immune responses as described herein. Similarly, agonistic antibodies to IL-1 zeta polypeptide are useful in upregulating IL-12 expression and are useful in enhancing the effects of Th1 mediated immune response as described herein.

Such an antibody may be employed in an in vitro procedure, or administered in vivo to inhibit a biological activity mediated by the entity that generated the antibody. Disorders caused or exacerbated (directly or indirectly) by the interaction of the polypeptides of the invention with the binding partner thus may be treated. A therapeutic method involves in vivo administration of a blocking antibody to a mammal in an amount effective in inhibiting a binding partner-mediated biological activity or a biological activity such as the inhibition of IL-12 and TNF expression. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface receptor, induce biological effects (e.g., transduction of biological signals) similar to the biological effects induced when IL-1 binds to cell surface IL-1 receptors. Agonistic antibodies may be used to activate IL-12 expression and treat disease associated with Th1 mediated pathways.

Compositions comprising an antibody that is directed against polypeptides of the invention, and a physiologically acceptable diluent, excipient, or carrier, are provided herein. Suitable components of such compositions are as described above for compositions containing polypeptides of the invention.

Also provided herein are conjugates comprising a detectable (e.g., diagnostic) or therapeutic agent, attached to the antibody. Examples of such agents are presented above. The conjugates find use in in vitro or in vivo procedures.

Because the IL-1 zeta polypeptides, and particularly the TDZ1 isoform, are active in IL-12 regulation and TNF regulation, inhibitors such as small molecule inhibitors of its function or its protein associations (or antisense or other inhibitors of its synthesis) will be useful in treating autoimmune and/or inflammatory disorders. Accordingly, IL-1 zeta polypeptides and fragments of IL-1 zeta polypeptides that are capable of upregulating IL-12 production or TNF production as described below, for example, are useful in screening assays to identify compounds and small molecules which inhibit (antagonize) functions and activities of IL-1 zeta polypeptide and described herein. Similarly, IL-1 zeta polypeptides and fragments of IL-1 zeta polypeptides that are capable of upregulating IL-12 production are useful in screening assays to identify compounds and small molecules which agonize or enhance IL-12 expression. Such compounds are useful as therapeutics for the herein described uses associated with enhanced IL-12 expression. (U.S. Pat. No. 5,674,483 and U.S. Pat. No. 5,928,636 which are incorporated herein by reference).

Thus, for example, polypeptides and polypeptide fragments of the invention may be used to identify antagonists and agonists from cells, cell-free preparations, chemical libraries, and natural product mixtures. The antagonists and agonists may be natural or modified substrates, ligands, enzymes, receptors, etc. of the polypeptides of the instant invention, or may be structural or functional mimetics of the polypeptides. Potential antagonists of the instant invention may include small molecules, peptides and antibodies that bind to and occupy a binding site of the inventive polypeptides or a binding partner thereof, causing them to be unavailable to bind to their natural binding partners and therefore preventing normal biological activity. Potential agonists include small molecules, peptides and antibodies which bind to the instant polypeptides or binding partners thereof, and elicit the same or enhanced biologic effects as those caused by the binding of the polypeptides of the instant invention.

Small molecule agonists and antagonists are usually less than 10 K molecular weight and may possess a number of physicochemical and pharmacological properties which enhance cell penetration, resist degradation and prolong their physiological half-lives (Gibbs, J., Pharmaceutical Research in Molecular Oncology, Cell, Vol. 79 (1994)). Antibodies, which include intact molecules as well as fragments such as Fab and F(ab')2 fragments, as well as recombinant molecules derived therefrom, may be used to bind to and inhibit the polypeptides of the instant invention by blocking the propagation of a signaling cascade. It is preferable that the antibodies are humanized, and more preferable that the antibodies are human. The antibodies of the present invention may be prepared by any of a variety of well-known methods.

Screening methods are known in the art and along with integrated robotic systems and collections of chemical compounds/natural products are extensively incorporated in high throughput screening so that large numbers of test compounds can be tested for antagonist or agonist activity within a short amount of time. These methods include homogeneous assay formats such as fluorescence resonance energy transfer, fluorescence polarization, time-resolved fluorescence resonance energy transfer, scintillation proximity assays, reporter gene assays, fluorescence quenched enzyme substrate, chromogenic enzyme substrate and electrochemiluminescence, as well as more traditional heterogeneous assay formats such as enzyme-linked immunosorbant assays (ELISA) or radioimmunoassays.

Homogeneous assays are mix-and-read style assays that are very amenable to robotic application, whereas heterogeneous assays require separation of free from bound analyte by more complex unit operations such as filtration, centrifugation or washing. These assays are utilized to detect a wide variety of specific biomolecular interactions and the inhibition thereof by small organic molecules, including protein-protein, receptor-ligand, enzyme-substrate, and so on. These assay methods and techniques are well known in the art (see, e.g., High Throughput Screening: The Discovery of Bioactive Substances, John P. Devlin (ed.), Marcel Dekker, New York, 1997 ISBN: 0-8247-0067-8). The screening assays of the present invention are amenable to high throughput screening of chemical libraries and are suitable for screening test compounds in order to identify small molecule drug candidates, antibodies, peptides, and other antagonists and/or agonists, natural or synthetic.

Thus, a method of the present invention includes screening a test compound to determine its effect on the ability of a polypeptide of this invention to increase or decrease IL-12 expression and/or TNF expression. Such a method involves co-culturing an IL-1 zeta polypeptide of this invention, particularly the TDZ1 isoform, and cells capable of expressing IL-12 and/or TNF (e.g. monocytes, PBMC) and analyzing the culture for IL-12 and/or TNF levels. If the level of expression differs from that level of expression that is observed in the absence of test compound, a test compound that affects IL-12 and/or TNF expression is identified. Polypeptides that are useful in the screening methods include the IL-1 zeta polypeptides of this invention and fragments of the IL-1 zeta polypeptides that upregulate IL-12 expression and/or TNF expression, particularly the TDZ1 isoform.

In one embodiment of a method for identifying molecules which inhibit or antagonize the polypeptides of this invention involves adding a test compound to a medium which contains cells that express the polypeptides of the instant invention; changing the conditions of the medium so that, but for the presence of the test compound, the polypeptides would be bound to their natural ligands, substrates or effector molecules, and observing the binding and stimulation or inhibition of a functional response. The activity of the cells which were contacted with the test compound may then be compared with the identical cells which were not contacted and antagonists and agonists of the polypeptides of the instant invention may be identified. The measurement of biological activity may be performed by a number of well-known methods such as measuring the amount of protein present (e.g. an ELISA) or measuring the protein's activity. A decrease in biological stimulation or activation indicates an antagonist. An increase indicates an agonist.

Another embodiment of the invention relates to uses of polypeptides of this invention to study cell signal transduction. Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adapter molecules that facilitate down stream signaling through protein-protein interaction following phosphorylation. Accordingly, these polypeptides and active fragments can be used as reagents to identify novel molecules involved in signal transduction pathways.

As therapeutics, inhibitors or agonists of IL-1 zeta activity can be administered to agonize or antagonize IL-1 zeta activity, thus providing useful immunoregulators. Various liposome-based compositions of the inventive polypeptides are envisioned herein.

Inhibitors and enhancers of the polypeptides or polypeptide fragments having biological activity are useful in treating a variety of medical conditions. IL-1 zeta polypeptides are associated with IL-12 production and dysregulation of IL-12 production, and thus agonists of IL-1 zeta polypeptides are useful for treating diseases and medical conditions that are therapeutically responsive to IL-12 expression. Such diseases and medical conditions include infectious diseases, such as HIV, Hepatitis B and Hepatitis C, papilloma, etc.; and, bacterial infections, including tuberculosis, salmonellosis, listeriousis; and, parasitic infections such as malaria, leishmaniasis and schistosomiasis. Agonists are also useful for treating dysregulated immune response, e.g. use as a vaccine (e.g. for use in connection with antigen such as for measles vaccination) or vaccine adjuvant, increased response to bacterial and viral infection, as just discussed, and as therapeutic immunotherapies including anticancer immunotherapy treatments. (See U.S. Pat. Nos. 6,086,876, and 6,168,923 both of which are incorporated herein by reference) In another embodiment, agonists of IL-1 zeta polypeptides can be administered in combination with other agents or cytokines for treating disease and medical conditions. For example, agonists can be administered in combination with IFN or IFN alpha. Antagonists of IL-1 zeta polypeptides are useful in treating certain types of immune system dysfunction associated with IL-12 dysregulation such as autoimmune diseases, inflammatory conditions, complications that are associated with bacterial infections that occur with increased IL-12 activity and conditions associated with increased expression or activity of IL-12. Thus, therapeutics discovered by screening IL-1 zeta polypeptides, the TDZ1 isoform and active fragments for agonistic or antagonistic activity have properties that make them suitable for use as: anti-inflammatory, anti-tumor or anti-cancer, anti-bacterial, and anti-viral.

Compositions of the present invention may contain a polypeptide or and antagonist or agonist in any form described herein, such as native proteins, variants, derivatives, oligomers, biologically active fragments of the compounds described herein, small molecules, antibodies, etc. In particular embodiments, the composition comprises peptides, small molecules, antibodies or oligomers comprising soluble polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, orally, intracranially or by inhalation. The term "parenteral" includes injection, e.g., by subcutaneous, intravenous, or intramuscular routes, also including localized administration, e.g., at a site of disease or injury (for example, intracoronary or intra tumor administration or injection into a joint undergoing an inflammatory reaction). Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Moreover, it has been found that DNA encoding a polypeptide can be administered to a mammal in such a way that it is taken up by cells, and expressed. The resultant protein will then be available to exert a therapeutic effect. Accordingly, compositions comprising nucleic acids in physiologically acceptable formulations are also contemplated. DNA may be formulated for injection, for example.

The following examples are provided to further illustrate particular embodiments of the invention, and are not to be construed as limiting the scope of the present invention.

EXAMPLE 1

Isolation of the IL-1 zeta and Xrec2 Nucleic Acids

Human IL-1 zeta nucleic acid sequence was obtained by sequencing EST IMAGE clone 1628761, accession #AI014548, which encoded a partial open reading frame (ORF). A number of cDNA libraries were screened with internal primers to determine the expression pattern of the polypeptide. After performing PCR using two internal primers of human IL-1 zeta sequence, the following cDNA libraries were positive for IL-1 zeta sequences: bone marrow stromal, human pancreatic tumor, and Raji. IL-1 zeta clones were isolated from human genomic DNA sequences, bone marrow stromal and human pancreatic tumor libraries, and sequenced.

Human Xrec2 sequences were obtained by high-throughput sequencing, PCR, and 5' RACE reactions. High-throughput shotgun sequencing of chromosome region Xp11 yielded sequences for exons 4-6 of Xrec2 (Genbank accession numbers AL031466 and AL031575). Similarly, sequence of chromosome region Xp22-164-166 (Genbank accession number AC005748) yielded sequences for exons 10-12 of Xrec2.

PCR performed on human brain first strand cDNA using primers within exons 5 and 11 generated sequence for exons 7-9. 5' RACE reactions were then performed using testis cDNA and nested primers within exon 4 to obtain exon 3 sequences which contained the predicted initiator methionine. Both PCR and the 5' RACE reactions were performed using standard protocols.

EXAMPLE 2

Use of Purified IL-1 zeta and Xrec2 Polypeptides

Polypeptide-specific ELISA:

Serial dilutions of IL-1 zeta- or Xrec2-containing samples (in 50 mM $NaHCO_3$, brought to pH 9 with NaOH) are coated onto Linbro/Titertek 96 well flat bottom E.I.A. microtitration plates (ICN Biomedicals Inc., Aurora, Ohio) at 100:1/well. After incubation at 4EC for 16 hours, the wells are washed six times with 200:1 PBS containing 0.05% Tween-20 (PBS-Tween). The wells are then incubated with $FLAG_7$-binding partner at 1 mg/ml in PBS-Tween with 5% fetal calf serum (FCS) for 90 minutes (100:1 per well), followed by washing as above. Next, each well is incubated with the anti-$FLAG_7$ (monoclonal antibody M2 at 1 mg/ml in PBS-Tween containing 5% FCS for 90 minutes (100:1 per well), followed by washing as above. Subsequently, wells are incubated with a polyclonal goat anti-mIgG1-specific horseradish peroxidase-conjugated antibody (a 1:5000 dilution of the commercial stock in PBS-Tween containing 5% FCS) for 90 minutes (100:1 per well). The HRP-conjugated antibody is obtained from Southern Biotechnology Associates, Inc., Birmingham, Ala. Wells then are washed six times, as above.

For development of the ELISA, a substrate mix [100:1 per well of a 1:1 premix of the TMB Peroxidase Substrate and Peroxidase Solution B (Kirkegaard Perry Laboratories, Gaithersburg, Md.)] is added to the wells. After sufficient color reaction, the enzymatic reaction is terminated by addition of 2 N $H_2SO_4$ (50:1 per well). Color intensity (indicating ligand receptor binding) is determined by measuring extinction at 450 nm on a V Max plate reader (Molecular Devices, Sunnyvale, Calif.).

EXAMPLE 3

Amino Acid Sequence

The amino acid sequence of IL-1 zeta and Xrec2 were determined by translation of the complete nucleotide sequences of SEQ ID NOs:1 and 2, respectively.

EXAMPLE 4

DNA and Amino Acid Sequences

The IL-1 zeta and Xrec2 nucleic acid sequences were determined by standard double stranded sequencing of the composite sequence of EST IMAGE clones (accession #AI014548 (IL-1 zeta) and # AL031575 and #AC005748 (Xrec2)), and of additional sequences obtained from PCR and 5' RACE reactions.

The nucleotide sequence of the isolated IL-1 zeta and Xrec2 DNA and the amino acid sequence encoded thereby, are presented in SEQ ID NOs:1-4. The sequence of the IL-1 zeta DNA fragment isolated by PCR corresponds to nucleotides 1 to 579 of SEQ ID NO:1, which encode amino acids 1 to 192 of SEQ ID NO:3; and the sequence of the Xrec2 DNA fragment also isolated by PCR corresponds to nucleotides 1 to 2088 of SEQ ID NO:2, which encode amino acids 1 to 698 of SEQ ID NO:4.

The amino acid sequences of SEQ ID NOs:3 and 4 bear significant homology to other known IL-1 ligand and receptor family members, respectively.

EXAMPLE 5

Monoclonal Antibodies that Bind Polypeptides of the Invention

This example illustrates a method for preparing monoclonal antibodies that bind IL-1 zeta. The same protocol can be used to produce monoclonal antibodies that bind Xrec2. Suitable immunogens that may be employed in generating such antibodies include, but are not limited to, purified IL-1 zeta polypeptide or an immunogenic fragment thereof such as the extracellular domain, or fusion proteins containing IL-1 zeta (e.g., a soluble IL-1 zeta/Fc fusion protein).

Purified IL-1 zeta can be used to generate monoclonal antibodies immunoreactive therewith, using conventional techniques such as those described in U.S. Pat. No. 4,411,993. Briefly, mice are immunized with IL-1 zeta immunogen emulsified in complete Freund's adjuvant, and injected in amounts ranging from 10-100 g subcutaneously or intraperitoneally. Ten to twelve days later, the immunized animals are boosted with additional IL-1 zeta emulsified in incomplete Freund's adjuvant. Mice are periodically boosted thereafter on a weekly to bi-weekly immunization schedule. Serum samples are periodically taken by retro-orbital bleeding or tail-tip excision to test for IL-1 zeta antibodies by dot blot assay, ELISA (Enzyme-Linked Immunosorbent Assay) or inhibition of IL-1 zeta receptor binding.

Following detection of an appropriate antibody titer, positive animals are provided one last intravenous injection of IL-1 zeta in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified IL-1 zeta by adaptations of the techniques disclosed in Engvall et al., (*Immunochem.* 8:871, 1971) and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c miceto produce ascites containing high concentrations of anti-IL-1 zeta monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to IL-1 zeta.

EXAMPLE 6

Northern Blot Analysis

The tissue distribution of IL-1 zeta and Xrec2 mRNA is investigated by Northern blot analysis, as follows. An aliquot of a radiolabeled probe is added to two different human multiple tissue Northern blots (Clontech, Palo Alto, Calif.; Biochain, Palo Alto, Calif.). The blots are hybridized in 10× Denhardts, 50 mM Tris pH 7.5, 900 mM NaCl, 0.1% Na pyrophosphate, 1% SDS, 200 µg/mL salmon sperm DNA. Hybridization is conducted overnight at 63EC in 50% formamide as previously described (March et al., *Nature* 315:641-647, 1985). The blots are then washed with 2×SSC, 0.1% SDS at 68EC for 30 minutes. The cells and tissues with the highest levels of IL-1 zeta and Xrec2 mRNA are determined by comparison to control probing with a β-actin-specific probe.

EXAMPLE 7

Binding Assay

Full length IL-1 zeta can be expressed and tested for the ability to bind IL-1 zeta receptors. The binding assay can be conducted as follows.

A fusion protein comprising a leucine zipper peptide fused to the N-terminus of a soluble IL-1 zeta polypeptide (LZ-IL-1 zeta) is employed in the assay. An expression construct is prepared, essentially as described for preparation of the FLAG[7](IL-1 zeta) expression construct in Wiley et al. (*Immunity*, 3:673-682, 1995; hereby incorporated by reference), except that DNA encoding the FLAG[7] peptide was replaced with a sequence encoding a modified leucine zipper that allows for trimerization. The construct, in expression vector pDC409, encodes a leader sequence derived from human cytomegalovirus, followed by the leucine zipper moiety fused to the N-terminus of a soluble IL-1 zeta polypeptide. The LZ-IL-1 zeta is expressed in CHO cells, and purified from the culture supernatant.

The expression vector designated pDC409 is a mammalian expression vector derived from the pDC406 vector described in McMahan et al. (*EMBO J.* 10:2821-2832, 1991; hereby incorporated by reference). Features added to pDC409 (compared to pDC406) include additional unique restriction sites in the multiple cloning site (mcs); three stop codons (one in each reading frame) positioned downstream of the mcs; and a T7 polymerase promoter, downstream of the mcs, that facilitates sequencing of DNA inserted into the mcs.

For expression of full length human IL-1 zeta protein, the entire coding region (i.e., the DNA sequence presented in SEQ ID NO:1) is amplified by polymerase chain reaction (PCR). The template employed in the PCR is the cDNA clone isolated from a (pancreatic tumor) cDNA library, as described in example 1. The isolated and amplified DNA is inserted into the expression vector pDC409, to yield a construct designated pDC409-IL-1 zeta.

LZ-IL-1 zeta polypeptide is employed to test the ability to bind to host cells expressing recombinant or endogenous IL-1 zeta receptors, as discussed above. Cells expressing IL-1 zeta receptor are cultured in DMEM supplemented with 10% fetal bovine serum, penicillin, streptomycin, and glutamine. Cells are incubated with LZ-IL-1 zeta (5 mg/ml) for about 1 hour. Following incubation, the cells are washed to remove unbound LZ-IL-1 zeta and incubated with a biotinylated anti-LZ monoclonal antibody (5 mg/ml), and phycoerythrin-conjugated streptavidin (1:400), before analysis by fluorescence-activated cell scanning (FACS). The cytometric analysis was conducted on a FACscan (Beckton Dickinson, San Jose, Calif.).

The cells expressing IL-1 zeta receptors showed significantly enhanced binding of LZ-IL-1 zeta, compared to the control cells not expressing IL-1 zeta receptors.

EXAMPLE 8

Obtaining TDZ.1, TDZ.2, and TDZ.3 and Tissue Distribution

In order to determine and study the relative abundance and tissue distribution of Tango-77 (WO 99/06426), an alternatively spliced form of IL-1 zeta, and IL-1 zeta, RT-PCR was performed. The primers used in the RT PCR were 5' primers specific for either Tango-77 exon #1 (see FIG. 1) or IL-1 zeta exon #1 (exons #3 in FIG. 1) in combination with a common 3' primer from the common final exon (exon #6 in FIG. 1). The PCR reactions were performed using first strand cDNA from multiple human tissue sources purchased from Clontech, Palo Alto, Calif. The PCR reaction generated PCR products that included the predicted size product and additional bands. In particular, three different sized PCR products were isolated and used to obtain sequence information from multiple tissue cDNAs. The sequences of these three products, SEQ ID NOs:5, 6, 7 and encoded amino acids of SEQ ID NO:8, 9, and 10, are splice variants. The organization the relationship of these splice variants are shown in FIG. 1 and discussed above. The splice variants are TDZ.1, TDZ.2, and TDZ.3 (Testis-Derived Zeta variants) because all three of them are expressed in testis. Testis is a common expression tissue. However, it is not the only expression tissue. Table II describes the results of the tissue expression study for Tango-77, IL-1 zeta, TDZ.1, TDZ.2, and TDZ.3. TDZ.1 and TDZ.2 contain exons 4, 5 and 6 which correspond to the last three exons of IL-1 zeta and correspond to the conserved structural domain of the molecule. As discussed above, when aligned with other members of the IL-1 family, exons 4, 5 and 6 are shown to contain many conserved residues within conserved structural motifs.

A polymorphism of Tango 77 in exon #2 of FIG. 1 is noted. In the isolated cDNAS a valine occurs in lieu of a glycine at the third residue of exon #2. In the Tango-77 sequence, the amino acid sequence is PAGSPLEP. In the polymorphism the sequence is PAVSPLEP.

TABLE II

TISSUE DISTRIBUTION OF FIL-1Z SPLICE VARIANTS

| Tissue | IL-1z | Tango-77 | TDZ.1 | TDZ.2 | TDZ.3 |
| --- | --- | --- | --- | --- | --- |
| kidney | − | − | + | − | − |
| pancreas | − | − | − | − | − |
| skeletal muscle | − | − | + | − | − |
| heart | − | + | − | − | − |
| testis | + | + | + | + | + |
| prostrate | + | − | + | − | − |
| spleen | − | − | − | − | − |
| ovary | − | + | + | − | − |
| thymus | − | − | − | − | − |
| colon | + | + | + | − | − |
| leukocytes | − | − | − | − | − |
| small intestine | − | + | + | − | − |
| liver | − | + | + | − | − |
| brain | + | − | − | − | − |
| placenta | + | + | + | − | + |
| lung | + | + | + | − | + |
| tonsil | − | + | + | − | − |
| fetal liver | + | + | + | − | − |
| lymph node | + | + | + | − | − |
| bone marrow | − | + | + | + | + |

EXAMPLE 9

IL-1 Zeta Polypeptide Induces TNF and IL-12 Secretion

The following assays were performed to study cytokine induction by IL-1 Zeta polypeptides. A protein of IL-1 zeta, TDZ.1 isoform, fused to a FLAG-poly His polypeptide at its C-terminus, was prepared and co-cultured with human monocytes. Varying concentrations of the TDZ.1 isoform were used with a lower level concentration of 5 nM. The culture was analyzed for cytokines and found to have increased levels of TNF-alpha and IL-12. This cytokine inducing activity was dose dependent.

The references cited herein are incorporated by reference herein in their entirety.

What is claimed is:

1. An isolated polypeptide comprising the amino sequence set forth in SEQ ID NO:8.

2. An oligomeric polypeptide comprising the polypeptide of claim 1.

3. An isolated polypeptide comprising a portion of the amino acid sequence set forth in SEQ ID NO: 8, wherein the amino acid sequence portion extends from an amino acid selected from the group consisting of any one of the amino acids at positions 41 to 51 of SEQ ID NO: 8, through the amino acid at position 218 of SEQ ID NO: 8.

4. The isolated polypeptide of claim 3, wherein the amino acid sequence portion extends from the amino acid at position 49 of SEQ ID NO: 8, through the amino acid at position 218 of SEQ ID NO: 8.

* * * * *

```
                        SEQUENCE LISTING

<160> NUMBER OF SEQ ID NOS: 15

<210> SEQ ID NO 1
<211> LENGTH: 579
<212> TYPE: DNA
<213> ORGANISM: Homo sapiens

<400> SEQUENCE: 1
atgtcaggct gtgataggag ggaaacagaa accaaaggaa agaacagctt taagaagcgc     60
ttaagaggtc caaaggtgaa gaacttaaac ccgaagaaat tcagcattca tgaccaggat    120
cacaaagtac tggtcctgga ctctgggaat ctcatagcag ttccagataa aaactacata    180
cgcccagaga tcttctttgc attagcctca tccttgagct cagcctctgc ggagaaagga    240
agtccgattc tcctgggggt ctctaaaggg gagttttgtc tctactgtga caaggataaa    300
ggacaaagtc atccatccct tcagctgaag aaggagaaac tgatgaagct ggctgcccaa    360
```

-continued

| | |
|---|---|
| aaggaatcag cacgccggcc cttcatctttt tatagggctc aggtgggctc ctggaacatg | 420 |
| ctggagtcgg cggctcaccc cggatggttc atctgcacct cctgcaattg taatgagcct | 480 |
| gttggggtga cagataaatt tgagaacagg aaacacattg aattttcatt tcaaccagtt | 540 |
| tgcaaagctg aaatgagccc cagtgaggtc agcgattag | 579 |

<210> SEQ ID NO 2
<211> LENGTH: 2091
<212> TYPE: DNA
<213> ORGANISM: Homo sapiens

<400> SEQUENCE: 2

| | |
|---|---|
| atgaaagctc cgattccaca cttgattctc ttatacgcta cttttactca gagtttgaag | 60 |
| gttgtgacca aaagaggctc cgccgatgga tgcactgact ggtctatcga tatcaagaaa | 120 |
| tatcaagttt tggtgggaga gcctgttcga atcaaatgtg cactcttta tggttatatc | 180 |
| agaacaaatt actcccttgc ccaaagtgct ggactcagtt tgatgtggta caaaagttct | 240 |
| ggtcctggag actttgaaga gccaatagcc tttgacggaa gtagaatgag caaagaagaa | 300 |
| gactccattt ggttccggcc aacattgcta caggacagtg gtctctacgc ctgtgtcatc | 360 |
| agaaactcca cttactgtat gaaagtatcc atctcactga cagtgggtga aatgacact | 420 |
| ggactctgct ataattccaa gatgaagtat tttgaaaaag ctgaacttag caaaagcaag | 480 |
| gaaatttcat gccgtgacat agaggatttt ctactgccaa ccagagaacc tgaaatcctt | 540 |
| tggtacaagg aatgcaggac aaaaacatgg aggccaagta ttgtattcaa agagatact | 600 |
| ctgcttataa gagaagtcag agaagatgac attggaaatt atacctgtga attaaaatat | 660 |
| ggaggctttg ttgtgagaag aactactgaa ttaactgtta cagcccctct gactgataag | 720 |
| ccacccaagc ttttgtatcc tatggaaagt aaactgacaa ttcaggagac ccagctgggt | 780 |
| gactctgcta atctaacctg cagagctttc tttgggtaca gcggagatgt cagtccttta | 840 |
| atttactgga tgaaggagaa aaatttatt gaagatctgg atgaaaatcg agtttgggaa | 900 |
| agtgacatta gaattcttaa ggagcatctt ggggaacagg aagtttccat ctcattaatt | 960 |
| gtggactctg tggaagaagg tgacttggga aattactcct gttatgttga aaatggaaat | 1020 |
| ggacgtcgac acgccagcgt tctccttcat aaacgagagc taatgtacac agtgaactt | 1080 |
| gctggaggcc ttggtgctat actcttgctg cttgtatgtt tggtgaccat ctacaagtgt | 1140 |
| tacaagatag aaatcatgct cttctacagg aatcattttg gagctgaaga gctcgatgga | 1200 |
| gacaataaag attatgatgc atacttatca taccccaaag tggatcctga ccagtggaat | 1260 |
| caagagactg gggaagaaga acgttttgcc cttgaaatcc tacctgatat gcttgaaaag | 1320 |
| cattatggat ataagttgtt tataccagat agagatttaa tcccaactgg aacatacatt | 1380 |
| gaagatgtgg caagatgtgt agatcaaagc aagcggctga ttattgtcat gaccccaaat | 1440 |
| tacgtagtta aagggggctg gagcatcttt gagctgaaaa ccagacttcg aaatatgctt | 1500 |
| gtgactggag aaattaaagt gattctaatt gaatgcagtg aactgagagg aattatgaac | 1560 |
| taccaggagg tggaggccct gaagcacacc atcaagctcc tgacggtcat taatggcat | 1620 |
| ggaccaaaat gcaacaagtt gaactccaag ttctggaaac gtttacagta tgaaatgcct | 1680 |
| tttaaggga tagaacccat tacacatgag caggctttag atgtcagtga caagggcct | 1740 |
| tttgggggagc tgcagactgt ctcggccatt tccatggccg cggccacctc cacagctcta | 1800 |
| gccactgccc atccagatct ccgttctacc tttcacaaca cgtaccattc acaaatgcgt | 1860 |
| cagaaaacact actaccgaag ctatgagtac gacgtacctc ctaccggcac cctgcctctt | 1920 |

-continued

```
acctccatag gcaatcagca tacctactgt aacatcccta tgacactcat caacgggcag    1980
cggccacaga caaaatcgag cagggagcag aatccagatg aggcccacac aaacagtgcc    2040
atcctgccgc tgttgccaag ggagaccagt atatccagtg tgatatggtg a             2091
```

<210> SEQ ID NO 3
<211> LENGTH: 192
<212> TYPE: PRT
<213> ORGANISM: Homo sapiens

<400> SEQUENCE: 3

```
Met Ser Gly Cys Asp Arg Arg Glu Thr Glu Thr Lys Gly Lys Asn Ser
1               5                   10                  15

Phe Lys Lys Arg Leu Arg Gly Pro Lys Val Lys Asn Leu Asn Pro Lys
            20                  25                  30

Lys Phe Ser Ile His Asp Gln Asp His Lys Val Leu Val Leu Asp Ser
        35                  40                  45

Gly Asn Leu Ile Ala Val Pro Asp Lys Asn Tyr Ile Arg Pro Glu Ile
    50                  55                  60

Phe Phe Ala Leu Ala Ser Ser Leu Ser Ser Ala Ser Ala Glu Lys Gly
65                  70                  75                  80

Ser Pro Ile Leu Leu Gly Val Ser Lys Gly Glu Phe Cys Leu Tyr Cys
                85                  90                  95

Asp Lys Asp Lys Gly Gln Ser His Pro Ser Leu Gln Leu Lys Lys Glu
            100                 105                 110

Lys Leu Met Lys Leu Ala Ala Gln Lys Glu Ser Ala Arg Arg Pro Phe
        115                 120                 125

Ile Phe Tyr Arg Ala Gln Val Gly Ser Trp Asn Met Leu Glu Ser Ala
    130                 135                 140

Ala His Pro Gly Trp Phe Ile Cys Thr Ser Cys Asn Cys Asn Glu Pro
145                 150                 155                 160

Val Gly Val Thr Asp Lys Phe Glu Asn Arg Lys His Ile Glu Phe Ser
                165                 170                 175

Phe Gln Pro Val Cys Lys Ala Glu Met Ser Pro Ser Glu Val Ser Asp
            180                 185                 190
```

<210> SEQ ID NO 4
<211> LENGTH: 696
<212> TYPE: PRT
<213> ORGANISM: Homo sapiens

<400> SEQUENCE: 4

```
Met Lys Ala Pro Ile Pro His Leu Ile Leu Leu Tyr Ala Thr Phe Thr
1               5                   10                  15

Gln Ser Leu Lys Val Val Thr Lys Arg Gly Ser Ala Asp Gly Cys Thr
            20                  25                  30

Asp Trp Ser Ile Asp Ile Lys Lys Tyr Gln Val Leu Val Gly Glu Pro
        35                  40                  45

Val Arg Ile Lys Cys Ala Leu Phe Tyr Gly Tyr Ile Arg Thr Asn Tyr
    50                  55                  60

Ser Leu Ala Gln Ser Ala Gly Leu Ser Leu Met Trp Tyr Lys Ser Ser
65                  70                  75                  80

Gly Pro Gly Asp Phe Glu Glu Pro Ile Ala Phe Asp Gly Ser Arg Met
                85                  90                  95

Ser Lys Glu Glu Asp Ser Ile Trp Phe Arg Pro Thr Leu Leu Gln Asp
            100                 105                 110
```

-continued

```
Ser Gly Leu Tyr Ala Cys Val Ile Arg Asn Ser Thr Tyr Cys Met Lys
        115                 120                 125
Val Ser Ile Ser Leu Thr Val Gly Glu Asn Asp Thr Gly Leu Cys Tyr
130                 135                 140
Asn Ser Lys Met Lys Tyr Phe Glu Lys Ala Glu Leu Ser Lys Ser Lys
145                 150                 155                 160
Glu Ile Ser Cys Arg Asp Ile Glu Asp Phe Leu Leu Pro Thr Arg Glu
                165                 170                 175
Pro Glu Ile Leu Trp Tyr Lys Glu Cys Arg Thr Lys Thr Trp Arg Pro
            180                 185                 190
Ser Ile Val Phe Lys Arg Asp Thr Leu Leu Ile Arg Glu Val Arg Glu
        195                 200                 205
Asp Asp Ile Gly Asn Tyr Thr Cys Glu Leu Lys Tyr Gly Gly Phe Val
210                 215                 220
Val Arg Arg Thr Thr Glu Leu Thr Val Thr Ala Pro Leu Thr Asp Lys
225                 230                 235                 240
Pro Pro Lys Leu Leu Tyr Pro Met Glu Ser Lys Leu Thr Ile Gln Glu
                245                 250                 255
Thr Gln Leu Gly Asp Ser Ala Asn Leu Thr Cys Arg Ala Phe Phe Gly
            260                 265                 270
Tyr Ser Gly Asp Val Ser Pro Leu Ile Tyr Trp Met Lys Gly Glu Lys
        275                 280                 285
Phe Ile Glu Asp Leu Asp Glu Asn Arg Val Trp Glu Ser Asp Ile Arg
    290                 295                 300
Ile Leu Lys Glu His Leu Gly Glu Gln Glu Val Ser Ile Ser Leu Ile
305                 310                 315                 320
Val Asp Ser Val Glu Glu Gly Asp Leu Gly Asn Tyr Ser Cys Tyr Val
                325                 330                 335
Glu Asn Gly Asn Gly Arg Arg His Ala Ser Val Leu Leu His Lys Arg
            340                 345                 350
Glu Leu Met Tyr Thr Val Glu Leu Ala Gly Gly Leu Gly Ala Ile Leu
        355                 360                 365
Leu Leu Leu Val Cys Leu Val Thr Ile Tyr Lys Cys Tyr Lys Ile Glu
370                 375                 380
Ile Met Leu Phe Tyr Arg Asn His Phe Gly Ala Glu Glu Leu Asp Gly
385                 390                 395                 400
Asp Asn Lys Asp Tyr Asp Ala Tyr Leu Ser Tyr Thr Lys Val Asp Pro
                405                 410                 415
Asp Gln Trp Asn Gln Glu Thr Gly Glu Glu Glu Arg Phe Ala Leu Glu
            420                 425                 430
Ile Leu Pro Asp Met Leu Glu Lys His Tyr Gly Tyr Lys Leu Phe Ile
        435                 440                 445
Pro Asp Arg Asp Leu Ile Pro Thr Gly Thr Tyr Ile Glu Asp Val Ala
    450                 455                 460
Arg Cys Val Asp Gln Ser Lys Arg Leu Ile Ile Val Met Thr Pro Asn
465                 470                 475                 480
Tyr Val Val Arg Arg Gly Trp Ser Ile Phe Glu Leu Glu Thr Arg Leu
                485                 490                 495
Arg Asn Met Leu Val Thr Gly Glu Ile Lys Val Ile Leu Ile Glu Cys
            500                 505                 510
Ser Glu Leu Arg Gly Ile Met Asn Tyr Gln Glu Val Glu Ala Leu Lys
        515                 520                 525
```

| | | | | | | | | | | | | |
|---|---|---|---|---|---|---|---|---|---|---|---|---|
| His | Thr | Ile | Lys | Leu | Leu | Thr | Val | Ile | Lys | Trp | His | Gly | Pro | Lys | Cys |
| | | 530 | | | | | 535 | | | | | 540 | | | |

Asn Lys Leu Asn Ser Lys Phe Trp Lys Arg Leu Gln Tyr Glu Met Pro
545                 550                 555                 560

Phe Lys Arg Ile Glu Pro Ile Thr His Glu Gln Ala Leu Asp Val Ser
            565                 570                 575

Glu Gln Gly Pro Phe Gly Glu Leu Gln Thr Val Ser Ala Ile Ser Met
        580                 585                 590

Ala Ala Ala Thr Ser Thr Ala Leu Ala Thr His Pro Asp Leu Arg
            595                 600                 605

Ser Thr Phe His Asn Thr Tyr His Ser Gln Met Arg Gln Lys His Tyr
    610                 615                 620

Tyr Arg Ser Tyr Glu Tyr Asp Val Pro Pro Thr Gly Thr Leu Pro Leu
625                 630                 635                 640

Thr Ser Ile Gly Asn Gln His Thr Tyr Cys Asn Ile Pro Met Thr Leu
            645                 650                 655

Ile Asn Gly Gln Arg Pro Gln Thr Lys Ser Ser Arg Glu Gln Asn Pro
        660                 665                 670

Asp Glu Ala His Thr Asn Ser Ala Ile Leu Pro Leu Leu Pro Arg Glu
            675                 680                 685

Thr Ser Ile Ser Ser Val Ile Trp
        690                 695

<210> SEQ ID NO 5
<211> LENGTH: 657
<212> TYPE: DNA
<213> ORGANISM: Homo sapiens

<400> SEQUENCE: 5

```
atgtcctttg tggggagaa ctcaggagtg aaaatgggct ctgaggactg ggaaaaagat      60 gaacccagt gctgcttaga agacccggct gtaagccccc tggaaccagg cccaagcctc     120
cccaccatga attttgttca cacaagtcca aggtgaaga acttaaaccc aagaaattc      180 agcattcatg accaggatca caagtactg gtcctggact ctgggaatct catagcagtt     240
ccagataaaa actacatacg cccagagatc ttctttgcat tagcctcatc cttgagctca     300
gcctctgcgg agaaaggaag tccgattctc ctggggtct ctaaagggga gttttgtctc     360
tactgtgaca aggataaagg acaaagtcat ccatcccttc agctgaagaa ggagaaactg     420
atgaagctgg ctgcccaaaa ggaatcagca cgccggccct tcatctttta tagggctcag     480
gtgggctcct ggaacatgct ggagtcggcg gctcaccccg atggttcat ctgcacctcc      540 tgcaattgta atgagcctgt tggggtgaca gataaatttg agaacaggaa acacattgaa     600
ttttcatttc aaccagtttg caaagctgaa atgagcccca gtgaggtcag cgattag        657
```

<210> SEQ ID NO 6
<211> LENGTH: 594
<212> TYPE: DNA
<213> ORGANISM: Homo sapiens

<400> SEQUENCE: 6

```
atgtcctttg tggggagaa ctcaggagtg aaaatgggct ctgaggactg ggaaaaagat      60 gaacccagt gctgcttaga aggtccaaag gtgaagaact taaaccccgaa gaaattcagc     120 attcatgacc aggatcacaa agtactggtc ctggactctg gaatctcat agcagttcca      180 gataaaaact acatacgccc agagatcttc tttgcattag cctcatcctt gagctcagcc     240
```

-continued

```
tctgcggaga aaggaagtcc gattctcctg ggggtctcta aggggagtt ttgtctctac      300 tgtgacaagg ataaaggaca aagtcatcca tcccttcagc tgaagaagga gaaactgatg      360
aagctggctg cccaaaagga atcagcacgc cggcccttca tcttttatag ggctcaggtg      420
ggctcctgga acatgctgga gtcggcggct caccccggat ggttcatctg cacctcctgc      480
aattgtaatg agcctgttgg ggtgacagat aaatttgaga acaggaaaca cattgaattt      540
tcatttcaac cagtttgcaa agctgaaatg agccccagtg aggtcagcga ttag            594
```

<210> SEQ ID NO 7
<211> LENGTH: 474
<212> TYPE: DNA
<213> ORGANISM: Homo sapiens

<400> SEQUENCE: 7

```
atgtcctttg tgggggagaa ctcaggagtg aaaatgggct ctgaggactg ggaaaaagat      60 gaacccagt gctgcttaga agagatcttc tttgcattag cctcatcctt gagctcagcc      120
tctgcggaga aaggaagtcc gattctcctg ggggtctcta aggggagtt ttgtctctac       180 tgtgacaagg ataaaggaca aagtcatcca tcccttcagc tgaagaagga gaaactgatg      240
aagctggctg cccaaaagga atcagcacgc cggcccttca tcttttatag ggctcaggtg      300
ggctcctgga acatgctgga gtcggcggct caccccggat ggttcatctg cacctcctgc      360
aattgtaatg agcctgttgg ggtgacagat aaatttgaga acaggaaaca cattgaattt      420
tcatttcaac cagtttgcaa agctgaaatg agccccagtg aggtcagcga ttag            474
```

<210> SEQ ID NO 8
<211> LENGTH: 218
<212> TYPE: PRT
<213> ORGANISM: Homo sapiens

<400> SEQUENCE: 8

```
Met Ser Phe Val Gly Glu Asn Ser Gly Val Lys Met Gly Ser Glu Asp
1               5                   10                  15

Trp Glu Lys Asp Glu Pro Gln Cys Cys Leu Glu Asp Pro Ala Val Ser
            20                  25                  30

Pro Leu Glu Pro Gly Pro Ser Leu Pro Thr Met Asn Phe Val His Thr
        35                  40                  45

Ser Pro Lys Val Lys Asn Leu Asn Pro Lys Lys Phe Ser Ile His Asp
    50                  55                  60

Gln Asp His Lys Val Leu Val Leu Asp Ser Gly Asn Leu Ile Ala Val
65                  70                  75                  80

Pro Asp Lys Asn Tyr Ile Arg Pro Glu Ile Phe Phe Ala Leu Ala Ser
                85                  90                  95

Ser Leu Ser Ser Ala Ser Ala Glu Lys Gly Ser Pro Ile Leu Leu Gly
            100                 105                 110

Val Ser Lys Gly Glu Phe Cys Leu Tyr Cys Asp Lys Asp Lys Gly Gln
        115                 120                 125

Ser His Pro Ser Leu Gln Leu Lys Lys Glu Lys Leu Met Lys Leu Ala
    130                 135                 140

Ala Gln Lys Glu Ser Ala Arg Arg Pro Phe Ile Phe Tyr Arg Ala Gln
145                 150                 155                 160

Val Gly Ser Trp Asn Met Leu Glu Ser Ala Ala His Pro Gly Trp Phe
                165                 170                 175

Ile Cys Thr Ser Cys Asn Cys Asn Glu Pro Val Gly Val Thr Asp Lys
            180                 185                 190
```

Phe Glu Asn Arg Lys His Ile Glu Phe Ser Phe Gln Pro Val Cys Lys
            195                 200                 205

Ala Glu Met Ser Pro Ser Glu Val Ser Asp
    210                 215

<210> SEQ ID NO 9
<211> LENGTH: 197
<212> TYPE: PRT
<213> ORGANISM: Homo sapiens

<400> SEQUENCE: 9

Met Ser Phe Val Gly Glu Asn Ser Gly Val Lys Met Gly Ser Glu Asp
1               5                   10                  15

Trp Glu Lys Asp Glu Pro Gln Cys Cys Leu Glu Gly Pro Lys Val Lys
            20                  25                  30

Asn Leu Asn Pro Lys Lys Phe Ser Ile His Asp Gln Asp His Lys Val
        35                  40                  45

Leu Val Leu Asp Ser Gly Asn Leu Ile Ala Val Pro Asp Lys Asn Tyr
    50                  55                  60

Ile Arg Pro Glu Ile Phe Phe Ala Leu Ala Ser Ser Leu Ser Ser Ala
65                  70                  75                  80

Ser Ala Glu Lys Gly Ser Pro Ile Leu Leu Gly Val Ser Lys Gly Glu
                85                  90                  95

Phe Cys Leu Tyr Cys Asp Lys Asp Lys Gly Gln Ser His Pro Ser Leu
            100                 105                 110

Gln Leu Lys Lys Glu Lys Leu Met Lys Leu Ala Ala Gln Lys Glu Ser
        115                 120                 125

Ala Arg Arg Pro Phe Ile Phe Tyr Arg Ala Gln Val Gly Ser Trp Asn
    130                 135                 140

Met Leu Glu Ser Ala Ala His Pro Gly Trp Phe Ile Cys Thr Ser Cys
145                 150                 155                 160

Asn Cys Asn Glu Pro Val Gly Val Thr Asp Lys Phe Glu Asn Arg Lys
                165                 170                 175

His Ile Glu Phe Ser Phe Gln Pro Val Cys Lys Ala Glu Met Ser Pro
            180                 185                 190

Ser Glu Val Ser Asp
        195

<210> SEQ ID NO 10
<211> LENGTH: 157
<212> TYPE: PRT
<213> ORGANISM: Homo sapiens

<400> SEQUENCE: 10

Met Ser Phe Val Gly Glu Asn Ser Gly Val Lys Met Gly Ser Glu Asp
1               5                   10                  15

Trp Glu Lys Asp Glu Pro Gln Cys Cys Leu Glu Glu Ile Phe Phe Ala
            20                  25                  30

Leu Ala Ser Ser Leu Ser Ser Ala Ser Ala Glu Lys Gly Ser Pro Ile
        35                  40                  45

Leu Leu Gly Val Ser Lys Gly Glu Phe Cys Leu Tyr Cys Asp Lys Asp
    50                  55                  60

Lys Gly Gln Ser His Pro Ser Leu Gln Leu Lys Lys Glu Lys Leu Met
65                  70                  75                  80

Lys Leu Ala Ala Gln Lys Glu Ser Ala Arg Arg Pro Phe Ile Phe Tyr
                85                  90                  95

```
Arg Ala Gln Val Gly Ser Trp Asn Met Leu Glu Ser Ala Ala His Pro
            100                 105                 110

Gly Trp Phe Ile Cys Thr Ser Cys Asn Cys Asn Glu Pro Val Gly Val
        115                 120                 125

Thr Asp Lys Phe Glu Asn Arg Lys His Ile Glu Phe Ser Phe Gln Pro
    130                 135                 140

Val Cys Lys Ala Glu Met Ser Pro Ser Glu Val Ser Asp
145                 150                 155

<210> SEQ ID NO 11
<211> LENGTH: 8
<212> TYPE: PRT
<213> ORGANISM: Artificial sequence
<220> FEATURE:
<223> OTHER INFORMATION: antigenic peptide used in fusion proteins

<400> SEQUENCE: 11

Asp Tyr Lys Asp Asp Asp Asp Lys
1               5

<210> SEQ ID NO 12
<211> LENGTH: 27
<212> TYPE: PRT
<213> ORGANISM: Artificial sequence
<220> FEATURE:
<223> OTHER INFORMATION: leucine zipper polypeptide

<400> SEQUENCE: 12

Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25

<210> SEQ ID NO 13
<211> LENGTH: 33
<212> TYPE: PRT
<213> ORGANISM: Artificial sequence
<220> FEATURE:
<223> OTHER INFORMATION: leucine zipper polypeptide

<400> SEQUENCE: 13

Arg Met Lys Gln Ile Glu Asp Lys Ile Glu Glu Ile Leu Ser Lys Ile
1               5                   10                  15

Tyr His Ile Glu Asn Glu Ile Ala Arg Ile Lys Lys Leu Ile Gly Glu
            20                  25                  30

Arg

<210> SEQ ID NO 14
<211> LENGTH: 8
<212> TYPE: PRT
<213> ORGANISM: Artificial sequence
<220> FEATURE:
<223> OTHER INFORMATION: polymorphic sequence from exon 2 of Tango 77

<400> SEQUENCE: 14

Pro Ala Gly Ser Pro Leu Glu Pro
1               5

<210> SEQ ID NO 15
<211> LENGTH: 8
<212> TYPE: PRT
<213> ORGANISM: Artificial sequence
<220> FEATURE:
```

```
<223> OTHER INFORMATION: polymorphic sequence from exon 2 of Tango 77

<400> SEQUENCE: 15

Pro Ala Val Ser Pro Leu Glu Pro
1               5
```